US012064576B2

(12) United States Patent
Howell et al.

(10) Patent No.: US 12,064,576 B2
(45) Date of Patent: Aug. 20, 2024

(54) GUIDEWIRE-MANAGEMENT DEVICES AND METHODS THEREOF

(71) Applicant: Bard Access Systems, Inc., Salt Lake City, UT (US)

(72) Inventors: Glade H. Howell, Draper, UT (US); Kevin Lloyd, Cottonwood Heights, UT (US); Jason R. Stats, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 495 days.

(21) Appl. No.: 17/200,566

(22) Filed: Mar. 12, 2021

(65) Prior Publication Data

US 2021/0283381 A1   Sep. 16, 2021

Related U.S. Application Data

(60) Provisional application No. 62/989,371, filed on Mar. 13, 2020.

(51) Int. Cl.
*A61M 25/09* (2006.01)

(52) U.S. Cl.
CPC ............ *A61M 25/09041* (2013.01); *A61M 2025/09066* (2013.01); *A61M 2025/09116* (2013.01)

(58) Field of Classification Search
CPC ............ A61M 25/09; A61M 25/09041; A61M 25/0111; A61M 25/002; A61M 25/0113; A61M 25/0668; A61M 2025/09175; A61M 2025/09116; A61M 2025/0034; A61B 50/30; A61B 50/00; A61B 2050/0065
See application file for complete search history.

(56) References Cited

U.S. PATENT DOCUMENTS 1,013,691 A   1/1912   Shields
3,225,762 A   12/1965  Guttman
(Continued)

FOREIGN PATENT DOCUMENTS

CN   202526749 U   11/2012
EP   0641571 A1   3/1995
(Continued)

OTHER PUBLICATIONS

PCT/US2021/061638 filed Dec. 2, 2021 International Search Report and Written Opinion dated Apr. 12, 2022.
(Continued)

*Primary Examiner* — Laura A Bouchelle
*Assistant Examiner* — Sarah Dympna Grasmeder
(74) *Attorney, Agent, or Firm* — Rutan & Tucker LLP

(57) ABSTRACT

Guidewire-management devices and systems thereof are disclosed herein. A guidewire-management device can include a guidewire, a first sleeve, and a second sleeve. The first sleeve can be configured for distally feeding the guidewire out of the guidewire-management device. The first sleeve can also be configured for proximally feeding the guidewire into the guidewire-management device. The second sleeve can be proximal of the first sleeve in the guidewire-management device. The second sleeve can be configured for feeding the guidewire in concert with the first sleeve. At least a length of the guidewire extending between the first sleeve and the second sleeve can be disposed within a sterile barrier configured to maintain sterility of the guidewire.

21 Claims, 17 Drawing Sheets

(56) References Cited

U.S. PATENT DOCUMENTS

Figure 1:
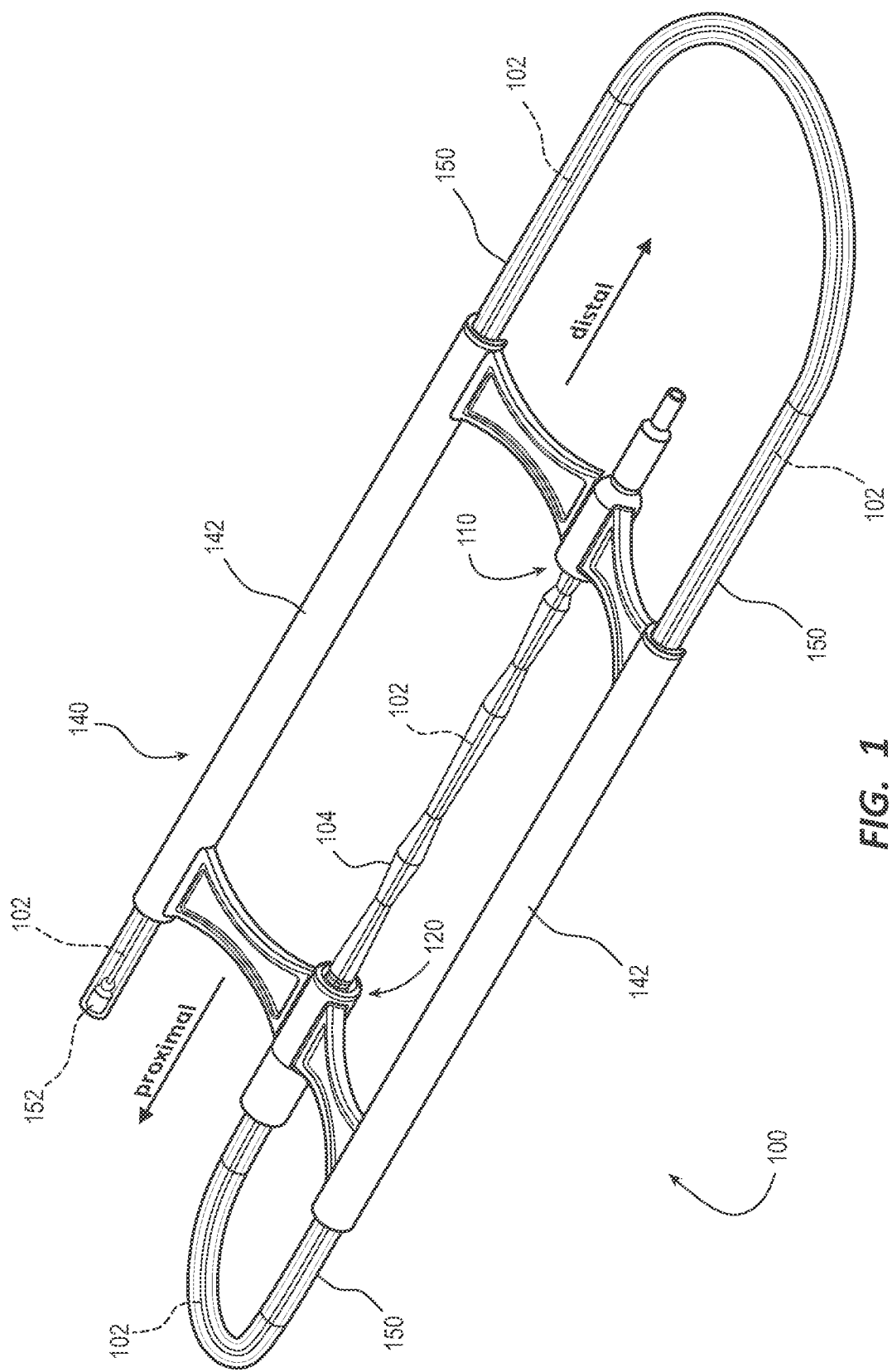

| | | |
|---|---|---|
| 3,890,976 A | 6/1975 | Bazell et al. |
| 4,051,849 A | 10/1977 | Poncy et al. |
| 4,205,675 A | 6/1980 | Vaillancourt |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,637,404 A | 1/1987 | Gessman |
| 4,840,613 A * | 6/1989 | Balbierz ............ A61M 25/0612 604/164.11 |
| 4,935,008 A | 6/1990 | Lewis, Jr. |
| 4,995,872 A | 2/1991 | Ferrara |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,120,317 A | 6/1992 | Luther |
| 5,188,593 A | 2/1993 | Martin |
| 5,195,962 A | 3/1993 | Martin et al. |
| 5,207,650 A | 5/1993 | Martin |
| 5,263,938 A * | 11/1993 | Orr ................. A61M 25/09041 604/171 |
| 5,267,958 A | 12/1993 | Buchbinder et al. |
| 5,273,042 A | 12/1993 | Lynch et al. |
| 5,282,479 A | 2/1994 | Havran |
| 5,295,970 A | 3/1994 | Clinton et al. |
| 5,306,247 A | 4/1994 | Pfenninger |
| 5,328,472 A | 7/1994 | Steinke et al. |
| 5,350,358 A | 9/1994 | Martin |
| 5,363,847 A | 11/1994 | Viera |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,420,882 A | 5/1995 | Black |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,683,370 A | 11/1997 | Luther et al. |
| 5,718,678 A | 2/1998 | Fleming, III |
| 5,772,636 A | 6/1998 | Brimhall et al. |
| 5,827,202 A | 10/1998 | Miraki et al. |
| 5,885,251 A | 3/1999 | Luther |
| 5,919,164 A | 7/1999 | Andersen |
| 5,947,940 A | 9/1999 | Beisel |
| 5,957,893 A | 9/1999 | Luther et al. |
| 6,123,084 A | 9/2000 | Jandak et al. |
| 6,206,849 B1 | 3/2001 | Martin et al. |
| 6,228,062 B1 | 5/2001 | Howell et al. |
| 6,475,187 B1 | 11/2002 | Gerberding |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,770 B2 | 12/2010 | Raulerson et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,579,484 B2 | 2/2017 | Barnell |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutilette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 11,285,301 B2 | 3/2022 | Ornelas Vargas et al. |
| 2002/0040231 A1 | 4/2002 | Wysoki |
| 2002/0198492 A1 | 12/2002 | Miller et al. |
| 2003/0036712 A1* | 2/2003 | Heh ................. A61M 25/09041 604/95.04 |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0193093 A1 | 9/2004 | Desmond |

(56) References Cited

U.S. PATENT DOCUMENTS

| | | |
|---|---|---|
| 2004/0230178 A1 | 11/2004 | Wu |
| 2005/0004554 A1 | 1/2005 | Osborne |
| 2005/0245847 A1 | 11/2005 | Schaeffer |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0064036 A1 | 3/2006 | Osborne et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0058839 A1 | 3/2008 | Nobles et al. |
| 2008/0091137 A1* | 4/2008 | Reavill ............ A61M 25/01 604/27 |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0105653 A1 | 4/2009 | Spenser et al. |
| 2009/0221961 A1 | 9/2009 | Tal et al. |
| 2009/0227900 A1 | 9/2009 | Kim et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0106057 A1 | 5/2011 | Hamboly |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0004665 A1 | 1/2012 | Defossez et al. |
| 2012/0041371 A1 | 2/2012 | Tal et al. |
| 2012/0065590 A1 | 3/2012 | Bierman et al. |
| 2012/0071857 A1 | 3/2012 | Goldfarb et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0220942 A1 | 8/2012 | Hall et al. |
| 2012/0283640 A1* | 11/2012 | Anderson ............ A61M 25/09 604/164.1 |
| 2012/0316500 A1 | 12/2012 | Bierman et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0045695 A1 | 2/2015 | Simpson et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297867 A1 | 10/2015 | Howell et al. |
| 2015/0297868 A1 | 10/2015 | Tal et al. |
| 2015/0320969 A1 | 11/2015 | Haslinger et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0074628 A1 | 3/2016 | Smith et al. |
| 2016/0082223 A1 | 3/2016 | Barnell |
| 2016/0114124 A1 | 4/2016 | Tal |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0014599 A1* | 1/2017 | Crisman ............ A61M 25/0113 |
| 2017/0035990 A1 | 2/2017 | Swift |
| 2017/0072165 A1 | 3/2017 | Lim et al. |
| 2017/0080189 A1 | 3/2017 | Tao et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0296799 A1 | 10/2018 | Horst et al. |
| 2018/0296804 A1 | 10/2018 | Bierman |
| 2019/0015646 A1 | 1/2019 | Matlock et al. |
| 2019/0046770 A1 | 2/2019 | Shields |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2021/0069471 A1 | 3/2021 | Howell |
| 2021/0085927 A1 | 3/2021 | Howell |
| 2021/0121661 A1 | 4/2021 | Howell |
| 2021/0121667 A1 | 4/2021 | Howell |
| 2021/0228843 A1 | 7/2021 | Howell et al. |
| 2021/0307854 A1 | 10/2021 | Bernhard et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0176082 A1 | 6/2022 | Mckinnon et al. |
| 2022/0193379 A1 | 6/2022 | Howell |
| 2022/0409275 A1 | 12/2022 | Hoang et al. |
| 2023/0128853 A1 | 4/2023 | Lindekugel et al. |
| 2023/0129318 A1 | 4/2023 | Lindekugel et al. |
| 2023/0277812 A1 | 9/2023 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2433670 A1 | 3/2012 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3205368 A1 | 8/2017 |
| EP | 3093038 B1 | 5/2019 |
| EP | 2260897 B1 | 9/2019 |
| GB | 1273547 A | 5/1972 |

(56) References Cited

FOREIGN PATENT DOCUMENTS

| | | |
|---|---|---|
| WO | 9306878 A1 | 4/1993 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 02/05886 A1 | 1/2002 |
| WO | 2003008020 A1 | 1/2003 |
| WO | 2003057272 A2 | 7/2003 |
| WO | 2003066125 A2 | 8/2003 |
| WO | 2006055288 A2 | 5/2006 |
| WO | 2006055780 A2 | 5/2006 |
| WO | 2006/096262 A2 | 9/2006 |
| WO | 2007046850 A2 | 4/2007 |
| WO | 2008005618 A2 | 1/2008 |
| WO | 2008033983 A1 | 3/2008 |
| WO | 2008092029 A2 | 7/2008 |
| WO | 2008/107869 A1 | 9/2008 |
| WO | 2008/131300 A2 | 10/2008 |
| WO | 2008131289 A2 | 10/2008 |
| WO | 2008133808 A1 | 11/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/146026 A1 | 8/2019 |
| WO | 2019199734 A1 | 10/2019 |
| WO | 2020069395 A1 | 4/2020 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2022/120068 A1 | 6/2022 |
| WO | 2022/133138 A2 | 6/2022 |
| WO | 2023069600 A1 | 4/2023 |
| WO | 2023069726 A1 | 4/2023 |
| WO | 2023167940 A1 | 9/2023 |

OTHER PUBLICATIONS

PCT/US2021/063903 filed Dec. 16, 2021, International Search Report and Written Opinion dated Jun. 28, 2022.
PCT/US2020/057202 filed Oct. 23, 2020 International Preliminary Report on Patentability dated Apr. 26, 2022.
PCT/US2020/057202 filed Oct. 23, 2020 International Search Report and Written Opinion dated Jan. 21, 2021.
PCT/US2021/022208 filed Mar. 12, 2021 International Search Report and Written Opinion dated Sep. 3, 2021.
PCT/US2022/047252 filed Oct. 20, 2022 International Search Report and Written Opinion dated Mar. 21, 2023.
PCT/US2022/047444 filed Oct. 21, 2022 International Search Report and Written Opinion dated Mar. 7, 2023.
U.S. Appl. No. 17/079,320, filed Oct. 23, 2020 Restriction Requirement dated Mar. 29, 2023.
PCT/US2023/014295 filed Mar. 1, 2023 International Search Report and Written Opinion dated Jun. 23, 2023.
U.S. Appl. No. 17/079,320, filed Oct. 23, 2020 Non-Final Office Action dated Jul. 28, 2023.
PCT/US2021/022226 filed Mar. 12, 2021 International Search Report and Written Opinion dated Oct. 21, 2021.
U.S. Appl. No. 17/200,630, filed Mar. 12, 2021 Non-Final Office Action dated Sep. 27, 2023.
U.S. Appl. No. 17/200,630, filed Mar. 12, 2021 Restriction Requirement dated Jul. 14, 2023.
U.S. Appl. No. 17/079,320, filed Oct. 23, 2020 Final Office Action dated Jan. 18, 2024.
U.S. Appl. No. 17/200,630, filed Mar. 12, 2021 Final Office Action dated Feb. 5, 2024.
Strittmatter, F., Eisel, M., Brinkmann, R., Cordes, J., Lange, B., & Sroka, R., "Laser Induced Lithotripsy: a Review, insight into laboratory work, and lessons learned." Translational Biophotonics, 2(1-2), e201900029. (2020).
Traxer, O., & Keller, E. X., "Thulium fiber laser: the new player for kidney stone treatment? A comparison with Holmium: YAG laser." World Journal of Urology, 38, 1883-1894. (2020).
U.S. Appl. No. 17/079,320, filed Oct. 23, 2020 Advisory Action dated Apr. 11, 2024.
U.S. Appl. No. 17/079,320, filed Oct. 23, 2020 Non-Final Office Action dated May 7, 2024.
U.S. Appl. No. 17/200,630, filed Mar. 12, 2021 Advisory Action dated May 10, 2024.
U.S. Appl. No. 17/200,630, filed Mar. 12, 2021 Non-Final Office Action dated Jun. 4, 2024.

* cited by examiner

GUIDEWIRE-MANAGEMENT DEVICES AND METHODS THEREOF

PRIORITY

This application claims the benefit of priority to U.S. Patent Application No. 62/989,371, filed Mar. 13, 2020, which is incorporated by reference in its entirety into this application.

BACKGROUND

A catheter is typically placed in a blood vessel of a patient using the Seldinger technique, which involves inserting a hollow needle into the blood vessel, inserting a guidewire into the needle, advancing the guidewire into the blood vessel, and removing the needle from the blood vessel leaving the guidewire in place. The catheter is then advanced over the guidewire until it is suitably placed with the patient's vasculature. The guidewire is then removed from the patient.

Guidewires for use in accordance with the Seldinger technique are typically packaged in a coiled-tube dispenser to keep the guidewires sterile and make handling the guidewires less cumbersome. However, inserting such a guidewire from a dispenser into a hollow needle requires two hands. In particular, one hand is required to hold both the needle and an engagement piece configured to guide the guidewire into the needle, while another hand is required to grip the guidewire and direct the guidewire from the dispenser into the needle. The more the guidewire is handled, the more opportunity for contamination or damage to the guidewire. In view of the foregoing, there is a need for better guidewire management in medical procedures such as those requiring the Seldinger technique.

Disclosed herein are guidewire-management devices and methods thereof that address the foregoing.

SUMMARY

Disclosed herein is a guidewire-management device including, in some embodiments, a guidewire, a first sleeve, and a second sleeve. The first sleeve is configured for distally feeding the guidewire out of the guidewire-management device. The first sleeve is also configured for proximally feeding the guidewire into the guidewire-management device. The second sleeve is proximal of the first sleeve in the guidewire-management device. The second sleeve is configured for feeding the guidewire in concert with the first sleeve. At least a length of the guidewire extending between the first sleeve and the second sleeve is disposed within a sterile barrier configured to maintain sterility of the guidewire. The sterile barrier is a splittable casing configured to split off the guidewire while distally feeding the guidewire out of the guidewire-management device.

In some embodiments, the first sleeve has a distal portion configured as a male connector with a Luer taper for connecting the first sleeve to a complementary female connector.

In some embodiments, the first sleeve is configured to straighten the guidewire when proximally feeding the guidewire into the guidewire-management device.

In some embodiments, the first sleeve includes a seal configured to block fluid from entering or escaping the guidewire-management device when proximally feeding the guidewire into the guidewire-management device.

In some embodiments, the first sleeve has a proximal portion including a bore configured to house a distal portion of the sterile barrier.

In some embodiments, the second sleeve has a distal portion including a bore configured to house a proximal portion of the sterile barrier.

In some embodiments, the second sleeve has a proximal portion including another bore configured to stop an end of the guidewire from completely passing through the second sleeve.

In some embodiments, the guidewire has a distal portion including a T-shaped tip configured to straighten as the tip of the guidewire enters the first sleeve when proximally feeding the guidewire into the guidewire-management device.

In some embodiments, the guidewire has a proximal portion including a ball end configured to stop the guidewire from completely passing through the second sleeve.

In some embodiments, the guidewire-management device is configured to redispose the splittable casing over the guidewire while proximally feeding the guidewire into of the guidewire-management device.

Also disclosed herein is a guidewire-management device including, in some embodiments, a handle, a guidewire, a first sleeve formed in a distal portion of the handle, a second sleeve formed in a proximal portion of the handle, and a thumb wheel disposed under the guidewire between the first sleeve and the second sleeve. At least a length of the guidewire extending between the first sleeve and the second sleeve is disposed within a sterile barrier configured to maintain sterility of the guidewire. The sterile barrier is a splittable casing configured to split off the guidewire while distally feeding the guidewire out of the guidewire-management device. The thumb wheel is configured to assist in distally feeding the guidewire out of the guidewire-management device by way of the first sleeve. The thumb wheel is also configured to assist in proximally feeding the guidewire into the guidewire-management device by way of the first sleeve.

In some embodiments, the first sleeve has a distal portion configured as a male connector with a Luer taper for connecting the first sleeve to a complementary female connector.

In some embodiments, the first sleeve is configured to straighten a T-shaped tip in a distal portion of the guidewire as the tip of the guidewire enters the first sleeve when proximally feeding the guidewire into the guidewire-management device.

In some embodiments, the second sleeve has a proximal portion including a bore with a constriction configured to capture a ball end of the guidewire and stop the guidewire from completely passing through the second sleeve.

In some embodiments, the splittable casing is over an entirety of the guidewire excepting that within or distal to the first sleeve.

In some embodiments, the guidewire-management device further includes a guidewire conduit coupled to the second sleeve and a casing conduit coupled to both a first split sleeve in the distal portion of the handle and a second split sleeve in the proximal portion of the handle. The guidewire conduit is configured to distally feed the guidewire into the second sleeve. The casing conduit is configured to collect therein the splittable casing that splits off the guidewire while distally feeding the guidewire out of the guidewire-management device.

In some embodiments, the handle includes a channel configured to hold the guidewire conduit therein when the guidewire conduit is in a coiled configuration.

In some embodiments, the guidewire-management device further includes a guidewire-casing conduit coupled to both the second sleeve and a first split sleeve in the distal portion of the handle. The guidewire-casing conduit is configured to distally feed the guidewire into the second sleeve. The guidewire-casing conduit is also configured to collect therein by way of the first split sleeve the splittable casing that splits off the guidewire while distally feeding the guidewire out of the guidewire-management device.

In some embodiments, a distal end of the splittable casing that splits off the guidewire is configured to chase a proximal end of the guidewire around the guidewire-casing conduit while distally feeding the guidewire out of the guidewire-management device.

In some embodiments, the handle includes a channel configured to hold the guidewire-casing conduit therein when the guidewire-casing conduit is in a coiled configuration.

In some embodiments, the guidewire-management device further includes a flexible membrane extending from the distal portion of the handle, over the thumb wheel, and to the proximal portion of the handle. The flexible membrane is configured to be pressed down onto the thumb wheel for distally feeding the guidewire out of the guidewire-management device or proximally feeding the guidewire into the guidewire-management device.

These and other features of the concepts provided herein will become more apparent to those of skill in the art in view of the accompanying drawings and following description, which describe particular embodiments of such concepts in greater detail. In addition, this application is related to U.S. patent application Ser. No. 17/079,320, filed Oct. 23, 2020, which is incorporated by reference in its entirety into this application.

DRAWINGS

FIG. 1 provides an isometric view of a first guidewire-management device in accordance with some embodiments.

Figure 2:
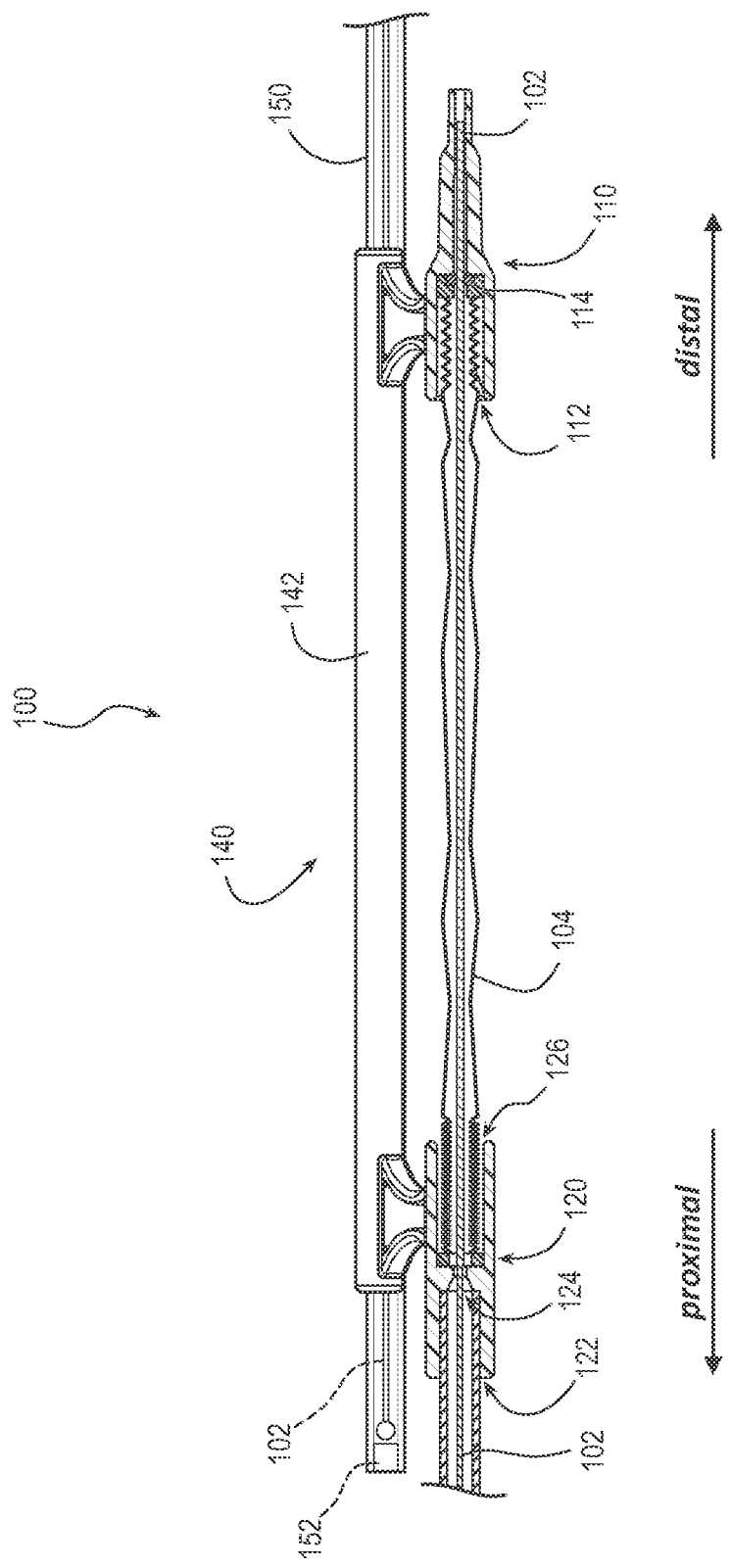

FIG. 2 provides a longitudinal cross section of the first guidewire-management device in accordance with some embodiments.

Figure 3:
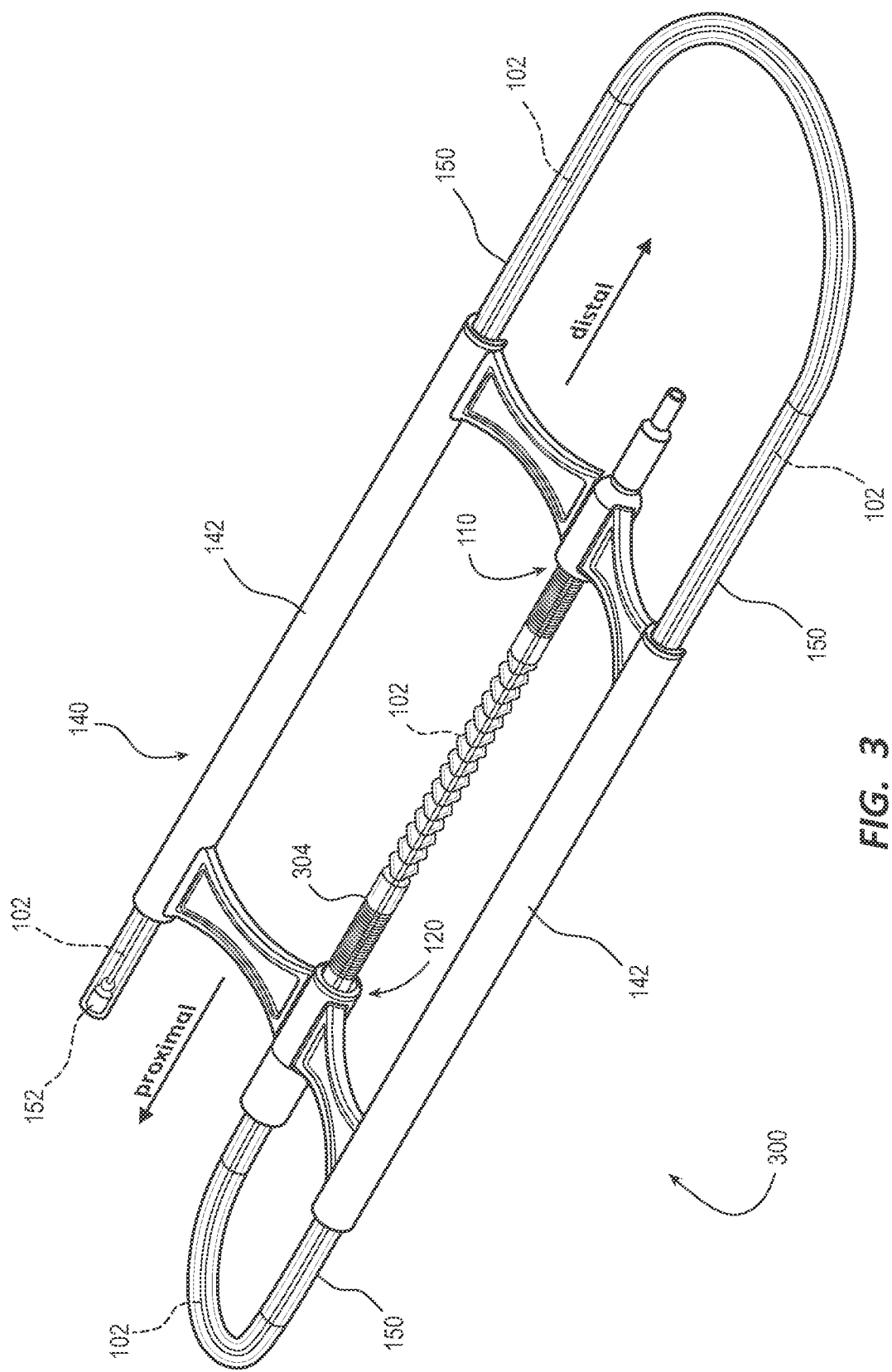

FIG. 3 provides an isometric view of a second guidewire-management device in accordance with some embodiments.

Figure 4:
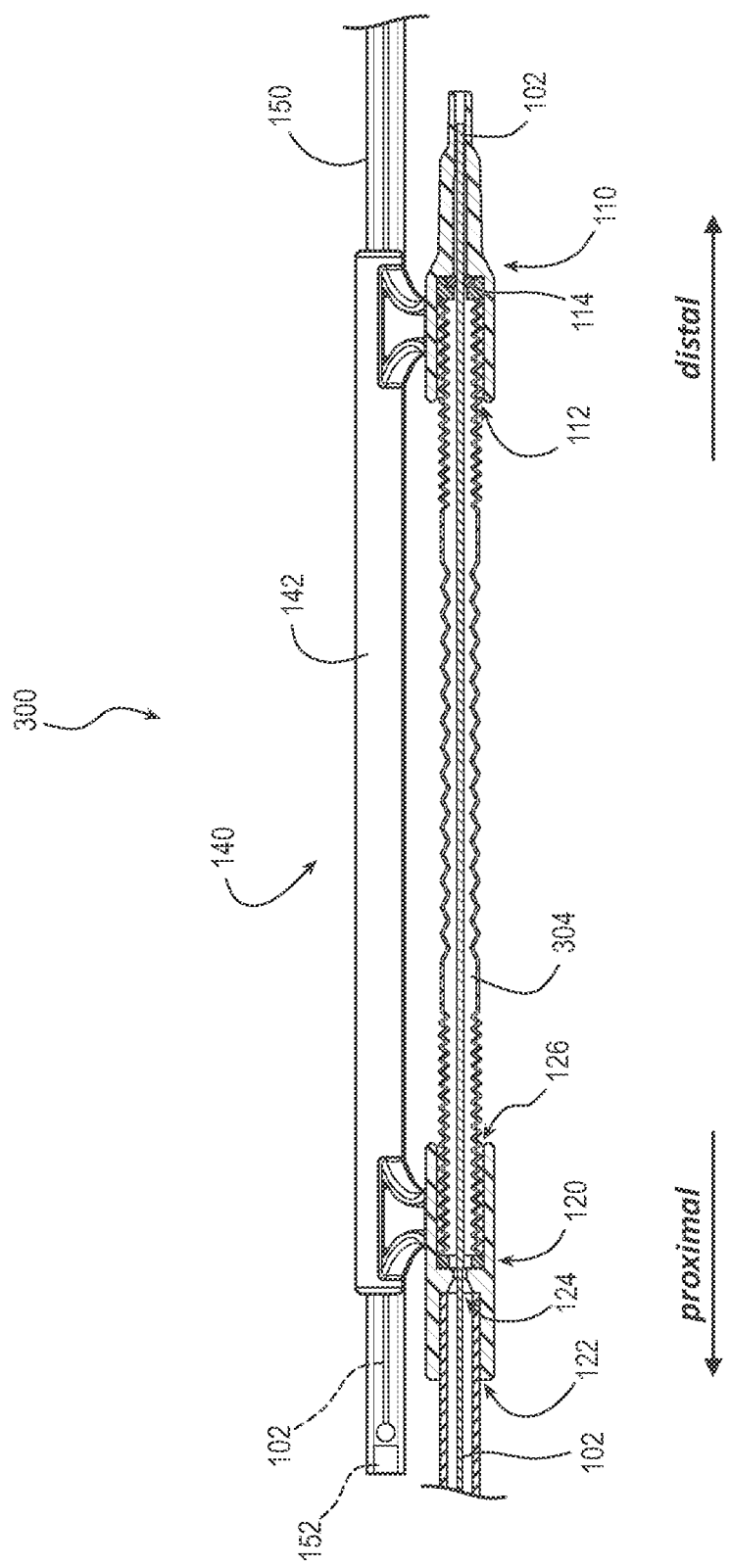

FIG. 4 provides a longitudinal cross section of the second guidewire-management device in accordance with some embodiments.

Figure 5:
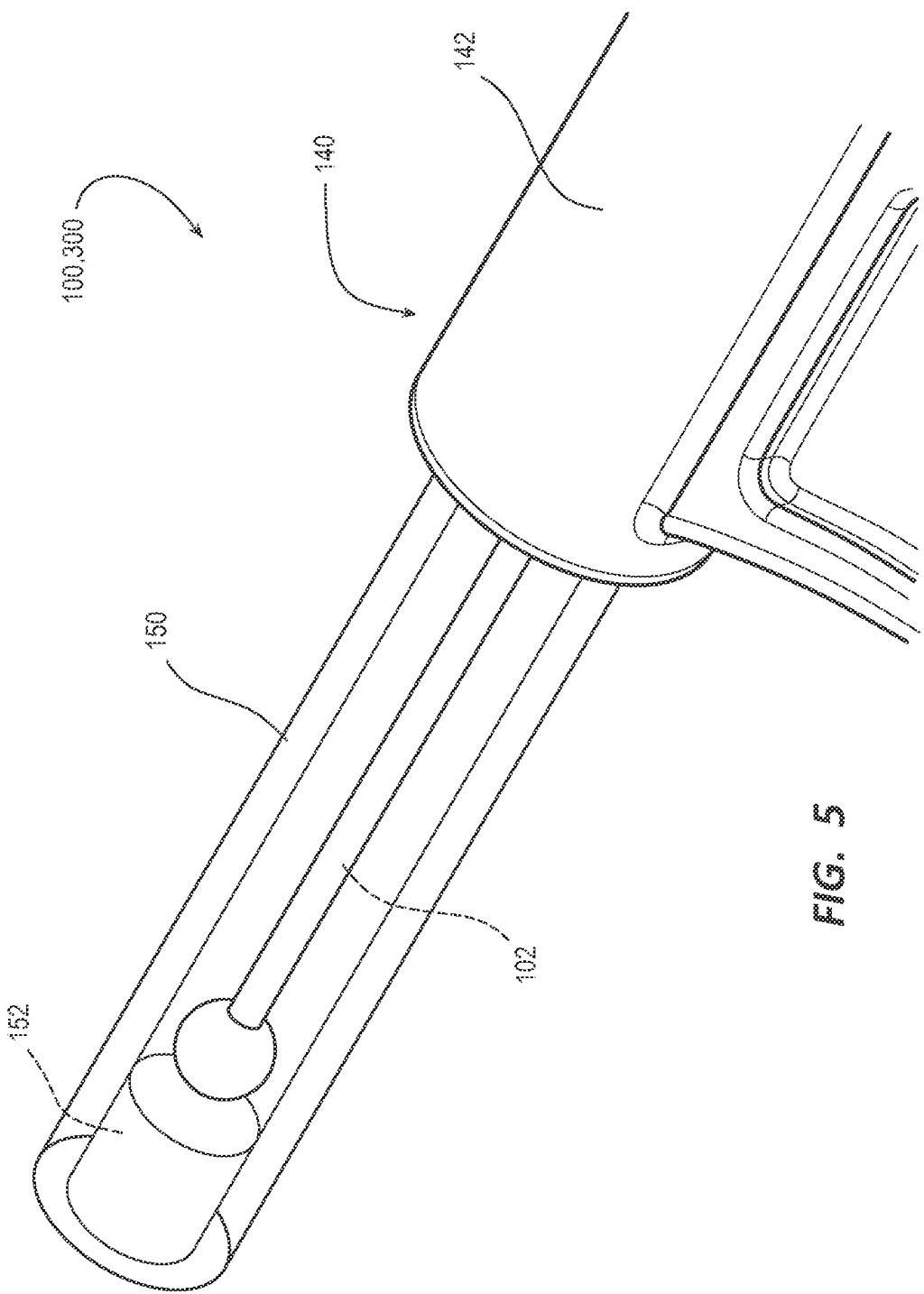

FIG. 5 provides a detailed view a ball end of a guidewire distal to a plug in a guidewire conduit in accordance with some embodiments.

Figure 6:
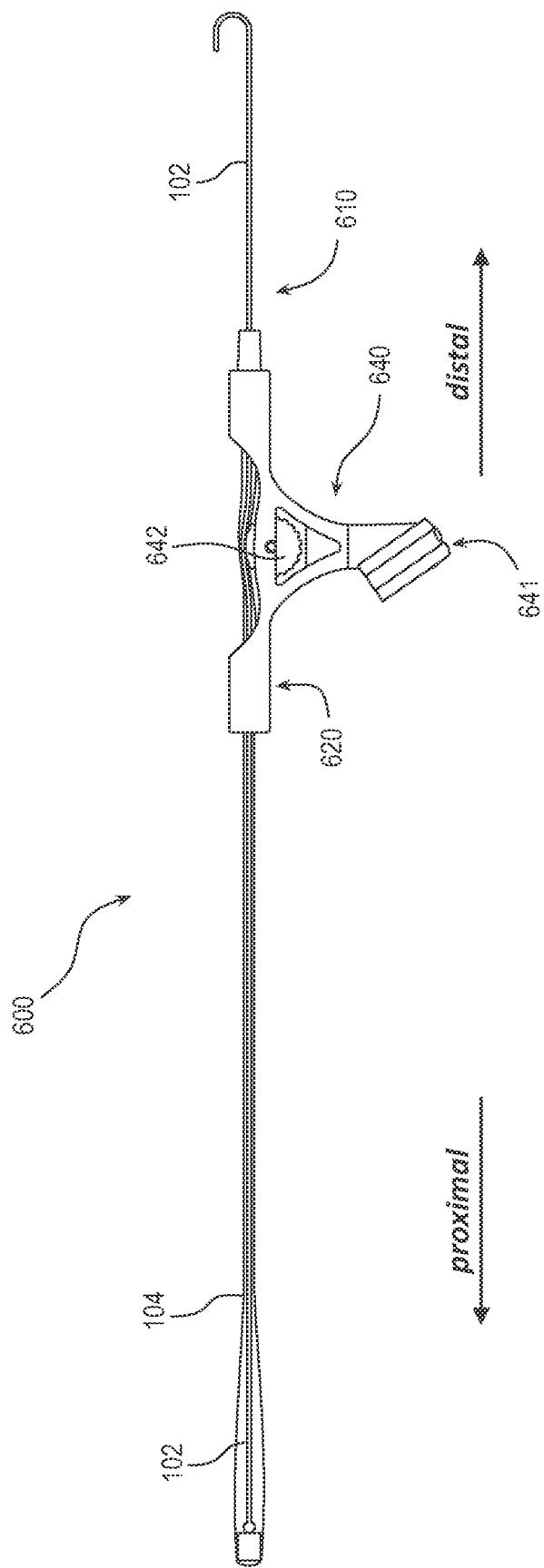

FIG. 6 provides a side view of a third guidewire-management device in accordance with some embodiments.

Figure 7:
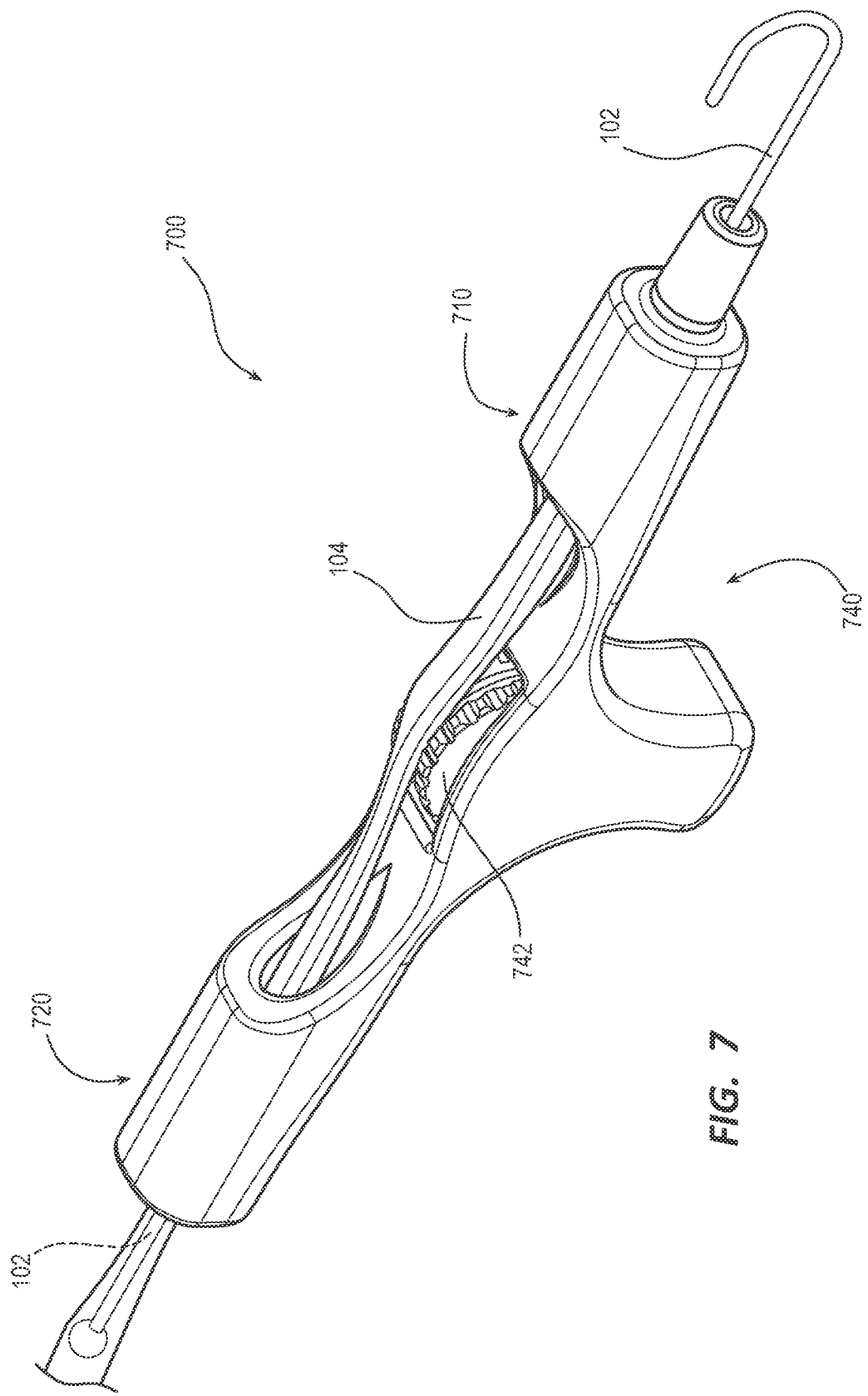

FIG. 7 provides an isometric view of a handle of a fourth guidewire-management device in accordance with some embodiments.

Figure 8:
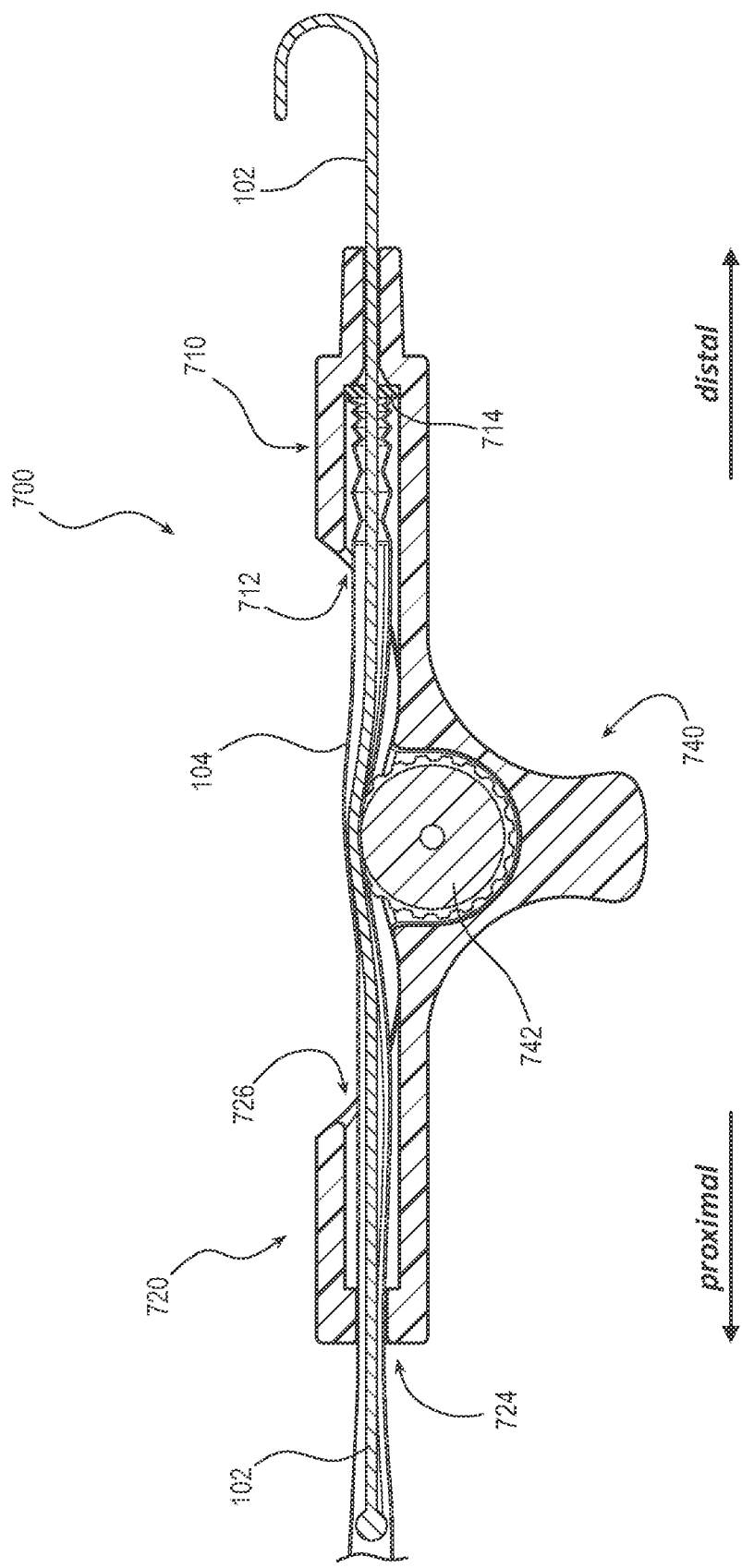

FIG. 8 provides a longitudinal cross section of the fourth guidewire-management device in accordance with some embodiments.

Figure 9:
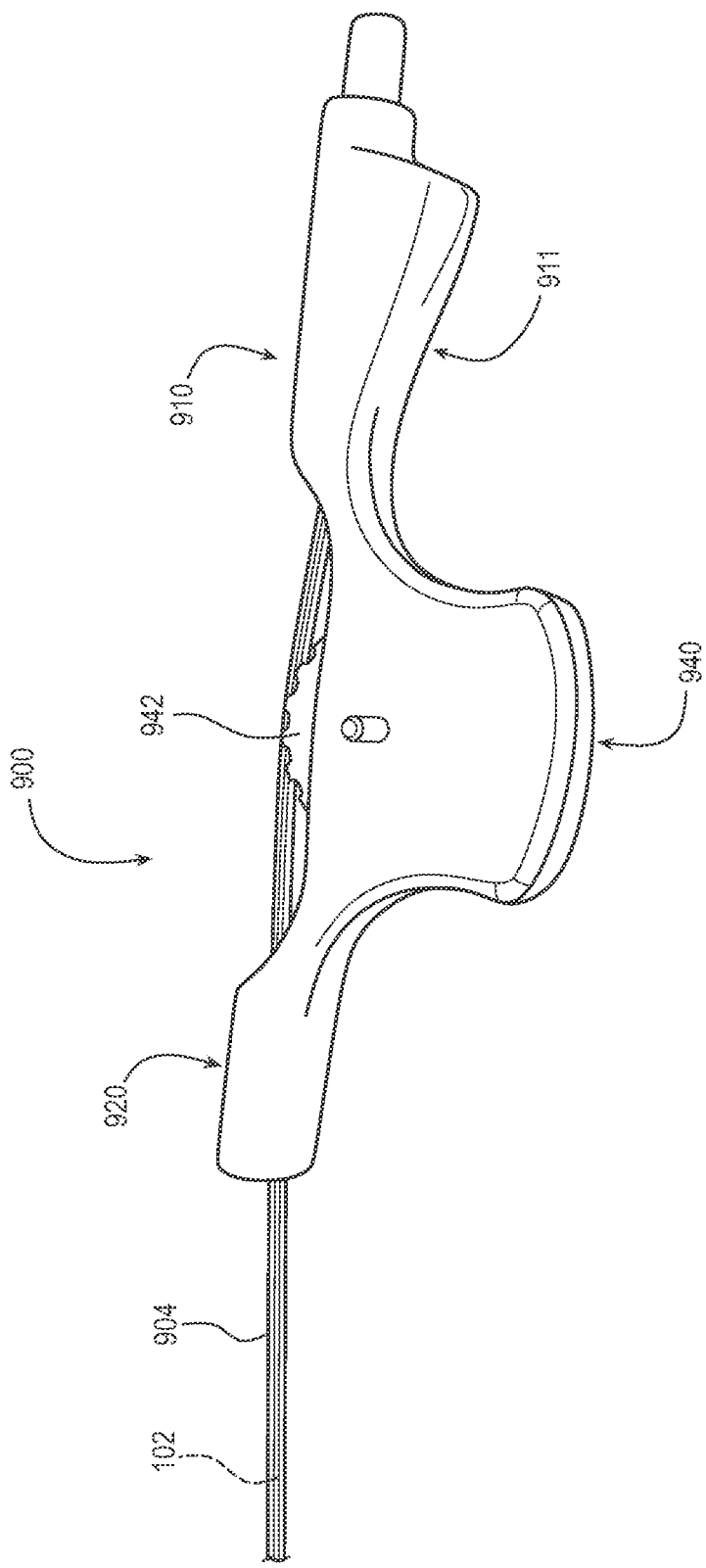

FIG. 9 provides a side view of a handle of a fifth guidewire-management device in accordance with some embodiments.

Figure 10:
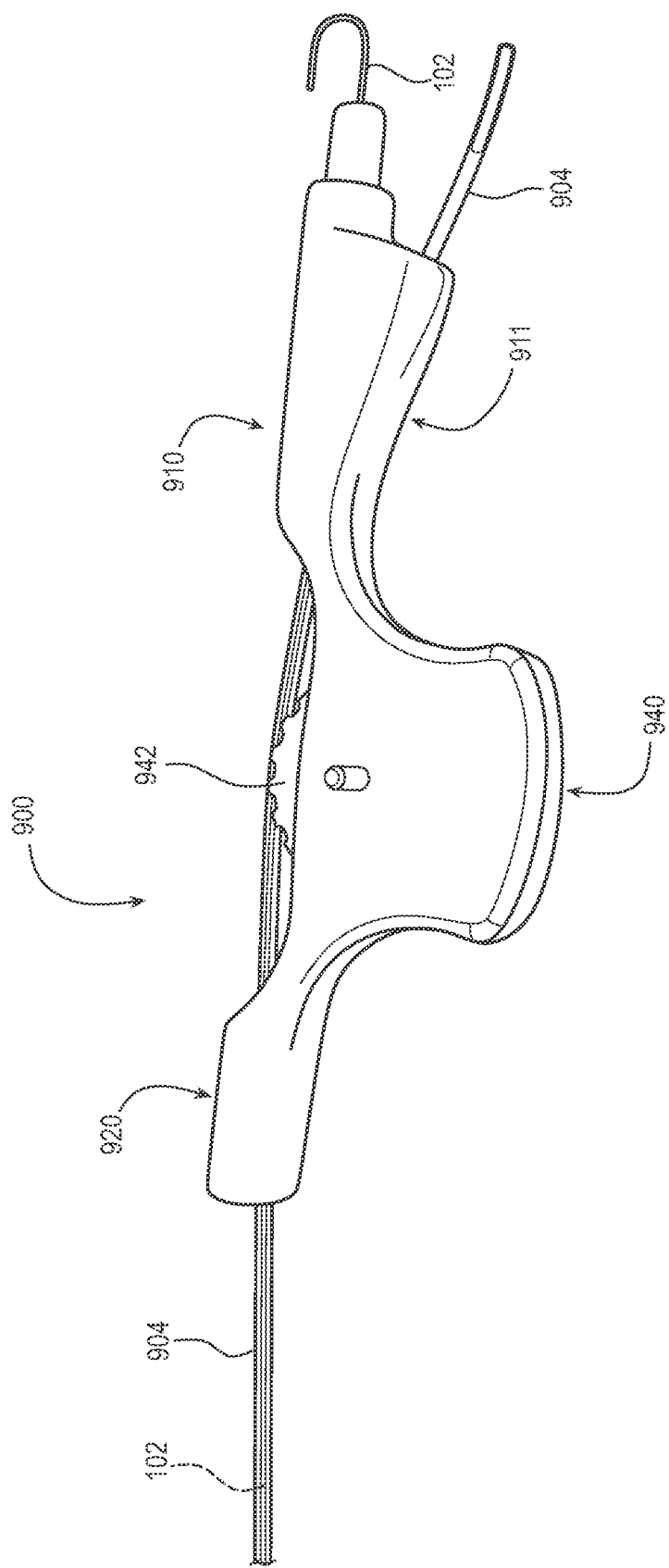

FIG. 10 provides the handle of a fifth guidewire-management device with a guidewire partially advanced out of the guidewire-management device in accordance with some embodiments.

Figure 11:
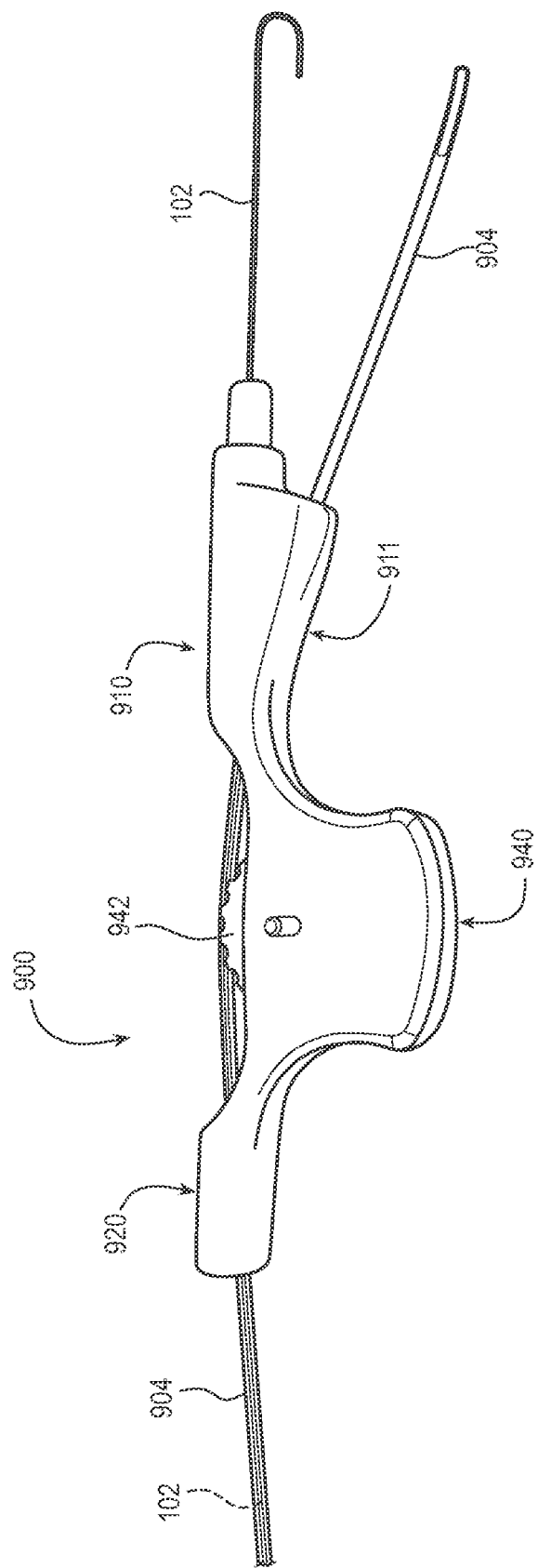

FIG. 11 provides the handle of the fifth guidewire-management device with the guidewire partially advanced out of the guidewire-management device farther than that shown in FIG. 10.

Figure 12:
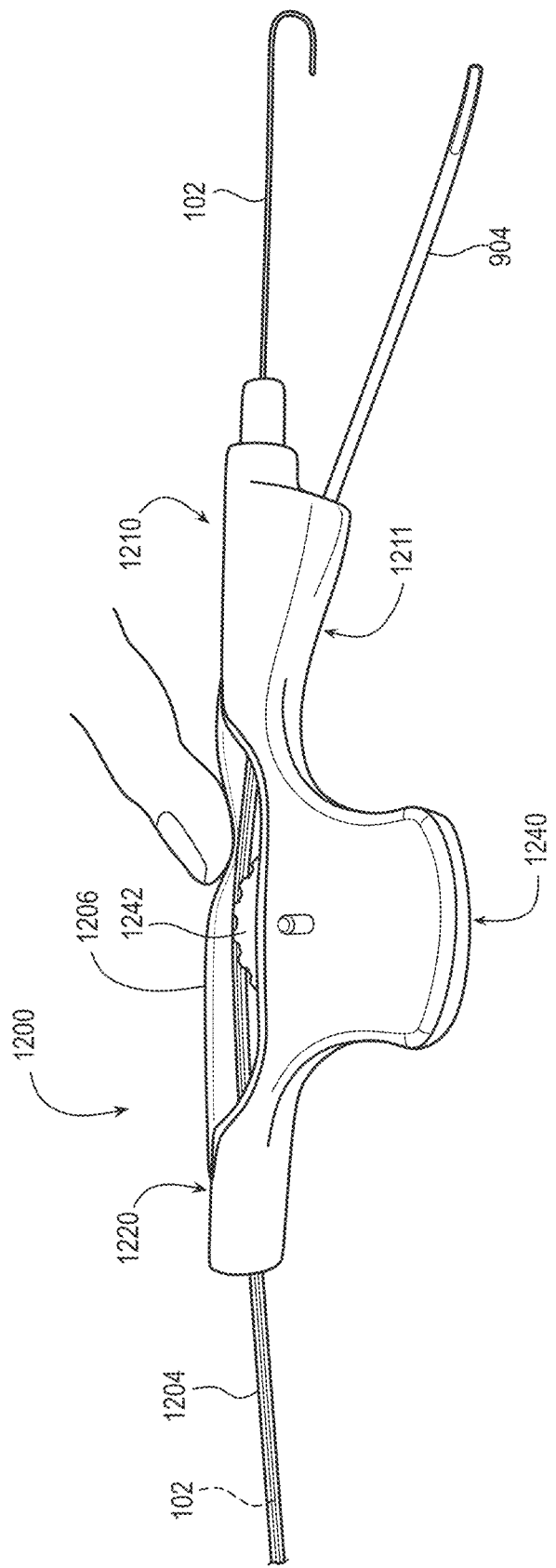

FIG. 12 provides a side view of a handle of a sixth guidewire-management device in accordance with some embodiments.

Figure 13:
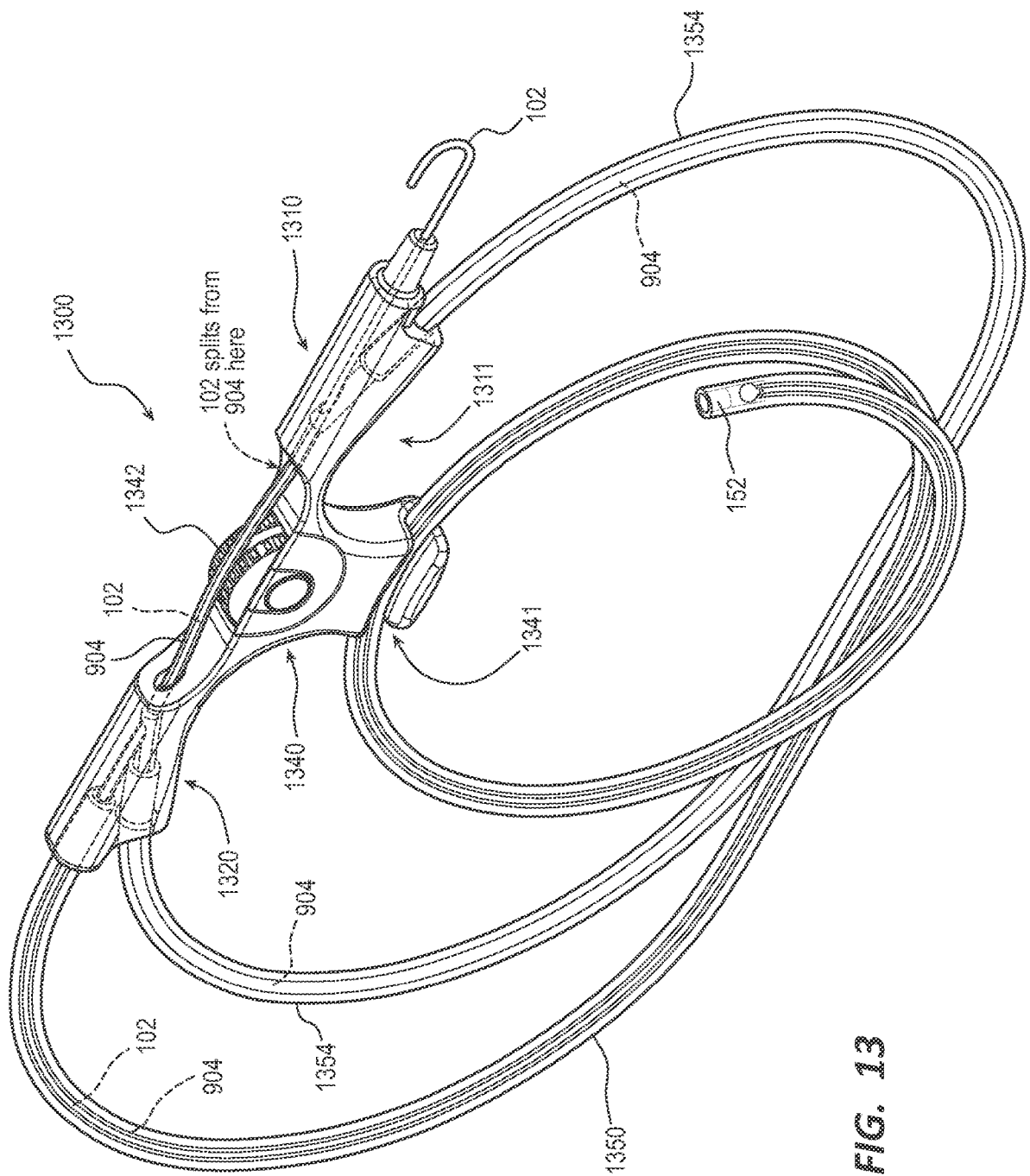

FIG. 13 provides an isometric view of a seventh guidewire-management device in accordance with some embodiments.

Figure 14:
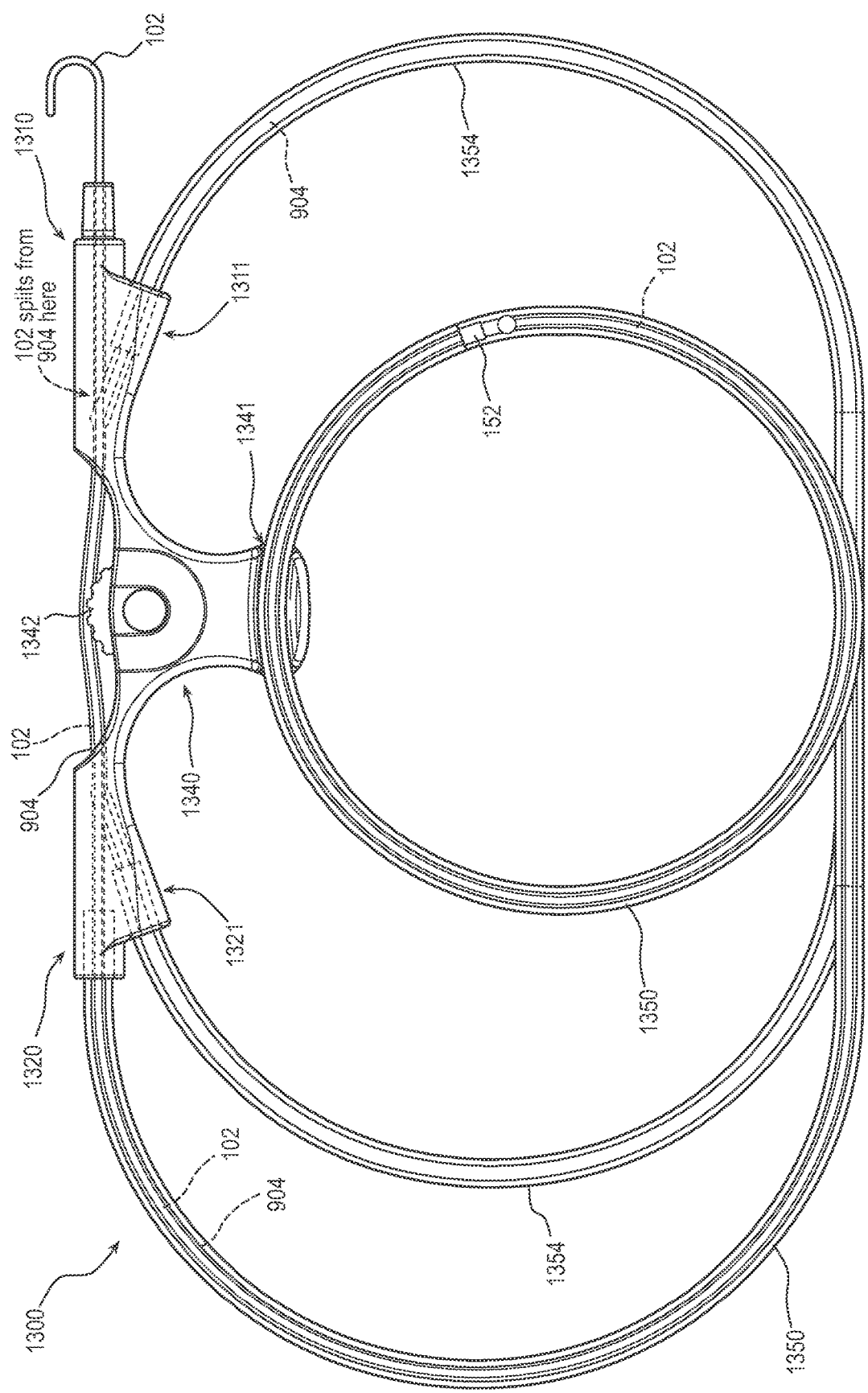

FIG. 14 provides a side view of the seventh guidewire-management device in accordance with some embodiments.

Figure 15:
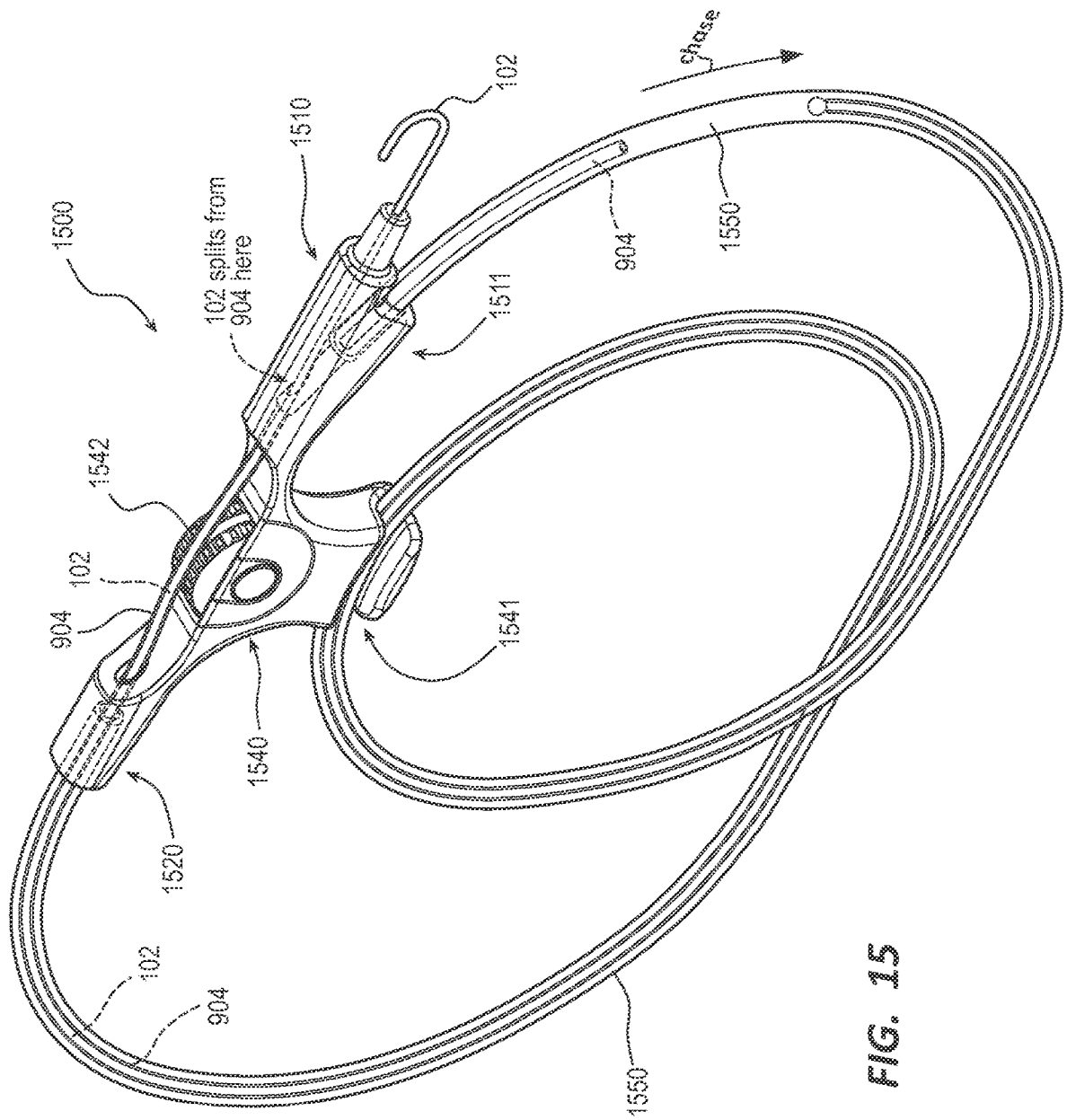

FIG. 15 provides an isometric view of an eighth guidewire-management device in accordance with some embodiments.

Figure 16:
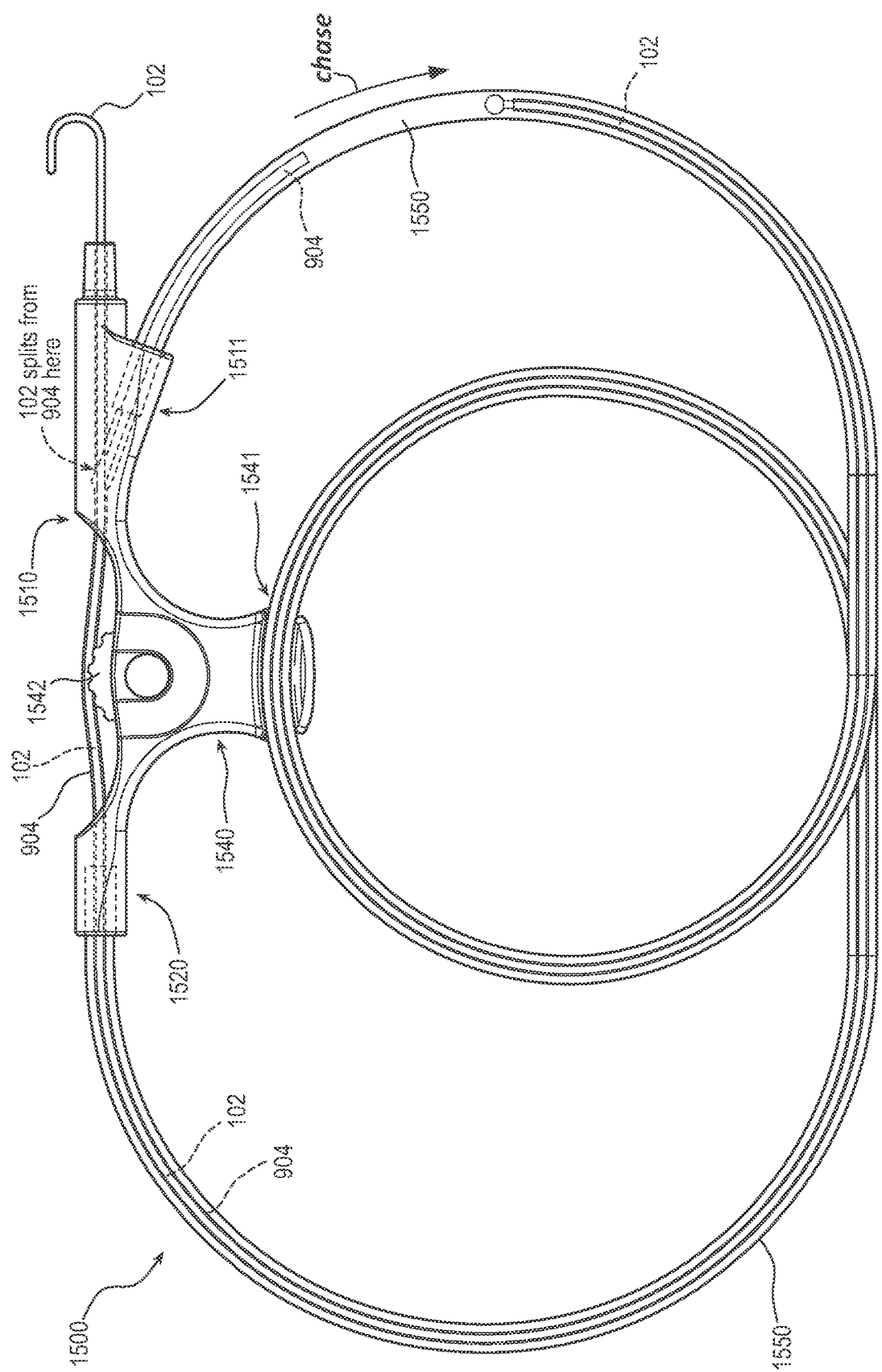

FIG. 16 provides a side view of the eighth guidewire-management device in accordance with some embodiments.

Figure 17:
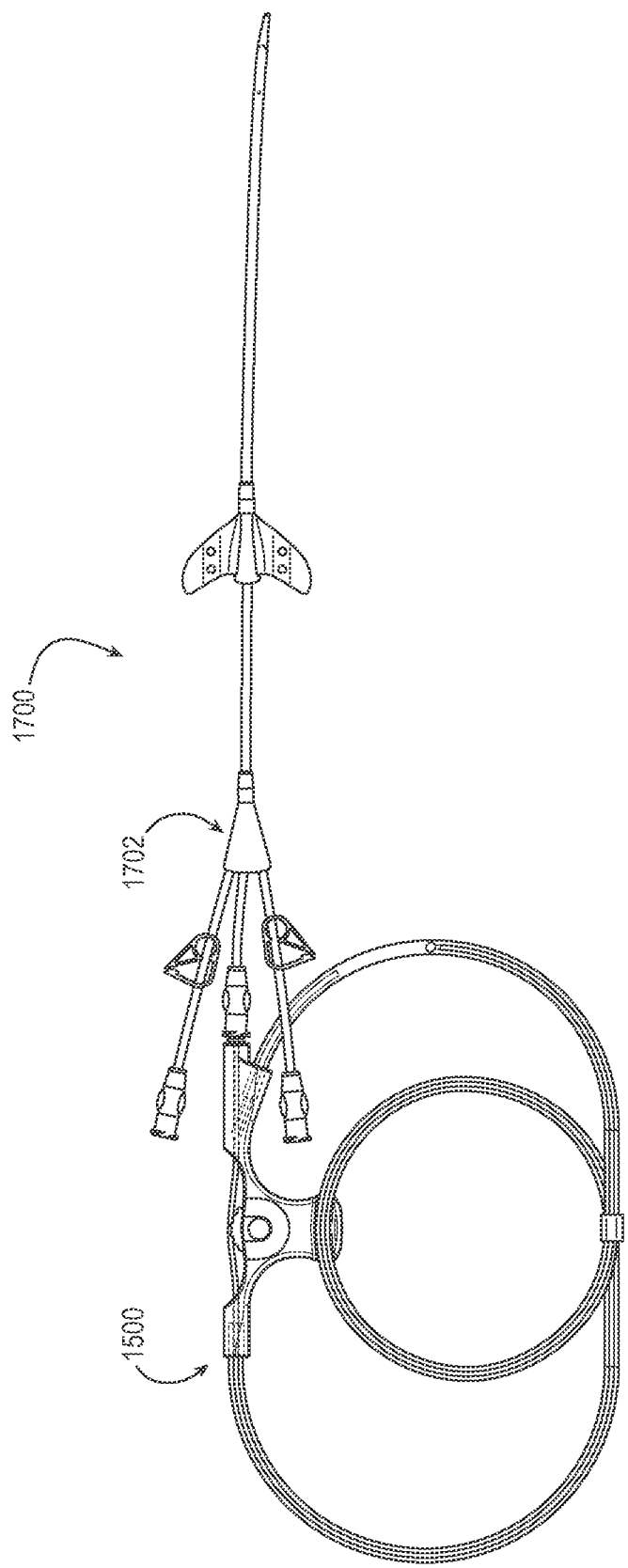

FIG. 17 provides a side view of the eighth guidewire-management device coupled with a catheter assembly in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for better guidewire management in medical procedures such as those requiring the Seldinger technique. Disclosed herein are guidewire-management devices and methods thereof that address the foregoing.

Guidewire-Management Devices

FIGS. 1-16 illustrate various guidewire-management devices, namely guidewire-management devices 100, 300, 600, 700, 900, 1200, 1300, and 1500. For expository expediency, guidewire-management devices 100, 300, 600, and 700 are initially described below with an emphasis on features in common with each other and many other guidewire management devices set forth herein. Such features can be identified among the various guidewire-management devices by identical reference numbers (e.g., guidewire 102), similar reference numbers (e.g., first sleeve 110, first sleeve 610, first sleeve 710, or the like, where the leading digits of the reference numbers are different to reflect the figures or embodiments associated with the features), description, or a combination thereof. Indeed, features in common among any group of guidewire-management devices of the various guidewire-management devices 100, 300, 600, 700, 900, 1200, 1300, and 1500 can be similarly identified. Subsequent to the initial description for the guidewire-management devices 100, 300, 600, and 700, the guidewire-management devices 100, 300, 600, 700, 900, 1200, 1300, and 1500 are individually or collectively described below with respect to some of the unique features thereof.

As shown, the guidewire-management device 100, 300, 600, or 700 includes a guidewire 102, a first sleeve 110, 610, or 710, and a second sleeve 120, 620, or 720.

The first sleeve 110, 610, or 710 is configured with a lumen for distally feeding, or advancing, the guidewire 102 out of the guidewire-management device 100, 300, 600, or 700. The first sleeve 110, 610, or 710 has a distal portion configured as a male connector with a Luer taper for connecting the first sleeve 110, 610, or 710 to a complementary female connector such as that of a hub of a hollow needle or a catheter. The male connector is configured such that when coupled to such a complementary female connector of, for example, the foregoing catheter, the guidewire-management device 100, 300, 600, or 700 forms a single unit with the catheter, thereby enabling the single unit to be held with one hand for guidewire management (e.g., distally feeding the guidewire 102 out of the guidewire-management device 100, 300, 600, or 700 into the catheter). (See FIG. 17.) The first sleeve 110, 610, or 710 also has a proximal portion including a bore 112, 612 (not shown), or 712 into which the lumen of the first sleeve 110, 610, or 710 opens. The bore 112, 612, or 712 is configured to house a distal portion of a sterile barrier 104 or 304 or collect the distal portion of the sterile barrier 104 or 304 when distally feeding the guidewire 102 out of the guidewire-management device 100, 300, 600, or 700.

The first sleeve 110, 610, or 710 is also configured for proximally feeding, or withdrawing, the guidewire 102 into the guidewire-management device 100, 300, 600, or 700. The first sleeve 110, 610, or 710 is configured to straighten the guidewire 102 such as a T-shaped tip thereof when proximally feeding the guidewire 102 into the guidewire-management device 100, 300, 600, or 700. (See FIGS. 7 and 8 for the T-shaped tip of the guidewire 102 in accordance with some embodiments.) The first sleeve 110, 610, or 710 can include a seal such as an 'O'-ring 114, 614 (not shown), or 714 configured to block fluid (e.g., blood) from entering the guidewire-management device 100, 300, 600, or 700 when proximally feeding the guidewire into the guidewire-management device 100, 300, 600, or 700. The seal, for example, the 'O'-ring 114, 614, or 714, is also configured to block fluid (e.g., air) from escaping the guidewire-management device 100, 300, 600, or 700 when proximally feeding the guidewire into the guidewire-management device 100, 300, 600, or 700, thereby minimizing or obviating risk of air embolism.

The second sleeve 120, 620, or 720 is proximal of the first sleeve 110, 610, or 710 in the guidewire-management device 100, 300, 600, or 700 such that at least a length of the guidewire 102 extends between the first sleeve 110, 610, or 710 and the second sleeve 120, 620, or 720. At least the length of the guidewire 102 extending between the first sleeve 110, 610, or 710 and the second sleeve 120, 620, or 720 is disposed within the sterile barrier 104 or 304.

The second sleeve 120, 620, or 720 is configured with a lumen for feeding the guidewire 102 in concert with the first sleeve 110, 610, or 710 such as distally feeding the guidewire 102 out of the guidewire-management device 100, 300, 600, or 700. The second sleeve 120, 620, or 720 has a proximal portion optionally including a bore 122 into which the lumen of the second sleeve 120, 620, or 720 opens. For example, the second sleeve 120 has the proximal portion including the bore 122, whereas the second sleeve 620 or 720 has the proximal portion without such a bore. Whether or not the second sleeve 120, 620, or 720 includes such a bore, the second sleeve 120, 620, or 720 further includes a constriction 124, a recess 724, or a similar stopping means for stopping an end of the guidewire 102 such as a ball or slug end thereof from completely passing through the second sleeve 120, 620, or 720 when distally feeding the guidewire 102 out of the guidewire-management device 100, 300, 600, or 700. Since the constriction 124, the recess 724, or the similar stopping means is configured to stop the end of the guidewire 102 from completely passing through the second sleeve 120, 620, or 720, the constriction 124, the recess 724, or the similar stopping means is also configured to stop the guidewire from completely passing through the guidewire-management device 100, 300, 600, or 700 and into a patient where the guidewire 102 can be lost.

The second sleeve 120, 620, or 720 is also configured for proximally feeding the guidewire 102 into of the guidewire-management device 100, 300, 600, or 700 in concert with the first sleeve 110, 610, or 710. The second sleeve 120, 620, 720 has a distal portion including a bore 126, 626 (not shown), or 726 into which the lumen of the second sleeve 120, 620, or 720 opens. The bore 126, 626, or 726 is configured to house a proximal portion of the sterile barrier 104 or 304 or collect the proximal portion of the sterile barrier 104 or 304 when proximally feeding the guidewire 102 into of the guidewire-management device 100, 300, 600, or 700.

The guidewire 102 has a distal portion and a proximal portion.

The distal portion of the guidewire 102 can include a T-shaped tip configured to straighten as the tip of the guidewire 102 enters the first sleeve 110, 610, or 710 when proximally feeding the guidewire 102 into the guidewire-management device 100, 300, 600, or 700. When distally feeding the guidewire 102 out of the guidewire-management device 100, 300, 600, or 700, the T-shaped tip is configured to reform the 'J' shape upon release from its constriction (e.g., the first sleeve 110, 610, or 710). If the first sleeve 110, 610, or 710 is connected to a complementary female connector such as that of a hub of a hollow needle, the tip of the guidewire 102 does not reform the 'J' shape until the tip is distally beyond the needle such as in a blood vessel.

The proximal portion of the guidewire 102 can include a ball end configured to stop the guidewire 102 from completely passing through the second sleeve 120, 620, or 720 on account of the constriction 124, the recess 724, or the similar stopping means when distally feeding the guidewire 102 out the guidewire-management device 100, 300, 600, or 700.

The sterile barrier 104 or 304 is configured to maintain sterility of the guidewire 102 while the guidewire 102 is disposed therein. Importantly, the guidewire never needs to be touched by a clinician during a procedure, thereby preserving the sterility of the guidewire 102 as well as ensuring the clinician remains free from contact with bodily fluids.

The sterile barrier 104 is a pleated bag. The sterile barrier 104, or the bag 104, is configured to unpleat as it is drawn from the second sleeve 120 of the guidewire-management device 100 or pass through the second sleeve 620 or 720 of the guidewire-management device 600 or 700 while distally feeding the guidewire 102 out of the guidewire-management device 100, 600, or 700. The bag 104 is also configured to pleat as it is inserted into the first sleeve 110, 610, or 710 while distally feeding the guidewire 102 out of the guidewire-management device 100, 600, or 700. Likewise, the bag 104 is configured to unpleat as it is drawn from the first sleeve 110, 610, or 710 while proximally feeding the guidewire 102 into the guidewire-management device 100, 600, or 700. The bag 104 is also configured to pleat as it is inserted into the second sleeve 120 of the guidewire-management device 100 or pass through the second sleeve 620 or 720 of the guidewire-management device 600 or 700 while proximally feeding the guidewire 102 into the guidewire-management device 100, 600, or 700.

Advantageously, in guidewire-management devices such as the guidewire-management devices 600 and 700, a combination of a length of the bag 104 and a sealed or valved end thereof is configured to stop the end (e.g., ball end) of the guidewire 102 from passing through what would otherwise be an opening in a proximal end of the bag 104. Stopping the end of the guidewire 102 from passing through such an opening prevents the tip of the guidewire 102 from completely passing through the first sleeve 110 and reforming the T-shaped tip when proximally feeding the guidewire 102 into the guidewire-management device 600 or 700.

A method for distally feeding, or advancing, the guidewire 102 out of the guidewire-management device 100, 600, or 700 is set forth below. A method for proximally feeding, or withdrawing, the guidewire 102 into the guidewire-management device 100, 600, or 700 is also set forth below.

The sterile barrier 304 is a bellowed boot. The sterile barrier 304, or the boot 304, is configured to iteratively stretch from an equilibrium state and relax back into the equilibrium state while distally feeding the guidewire 102 out of the guidewire-management device 300. Likewise, the boot 304 is configured to iteratively stretch from an equilibrium state and relax back into the equilibrium state while proximally feeding the guidewire 102 into the guidewire-management device 300.

A method for distally feeding, or advancing, the guidewire 102 out of the guidewire-management device 300 is set forth below. A method for proximally feeding, or withdrawing, the guidewire 102 into the guidewire-management device 300 is also set forth below.

While not shown for any guidewire-management device of the guidewire-management devices 100, 300, 600, and 700, the sterile barrier 104 or 304 can alternatively be a splittable casing 904 over an entirety of the guidewire 102 or at least most of the guidewire 102, for example, excepting that within or distal to the first sleeve 110, 610, or 710. The splittable casing 904 is configured to split off the guidewire 102 while distally feeding the guidewire 102 out of a guidewire-management device. (See, for example, the guidewire-management devices 900, 1200, 1300, and 1500.) Some of the foregoing guidewire-management devices (e.g., the guidewire-management devices 1300 and 1500) are configured to insert the guidewire 102 into the splittable casing 904 while proximally feeding the guidewire 102 into the guidewire-management devices. The splittable casing 904 can include graduated markings thereon configured to indicate a length of the guidewire 102 from the tip thereof.

Adverting to FIGS. 1-4 to describe some of the unique features of least the guidewire-management devices 100 and 300, the guidewire-management devices 100 and 300 include the guidewire 102, a frame 140 including a pair of tubular rails 142, a guidewire conduit 150 threaded through the pair of tubular rails 142, the first sleeve 110 mounted on struts between each rail of the pair of tubular rails 142, and the second sleeve 120 mounted on struts between each rail of the pair of tubular rails 142 proximal of the first sleeve 110. At least a portion of the guidewire 102 is disposed within the guidewire conduit 150.

The guidewire conduit 150 can be opaque or translucent depending upon a chosen polymeric material. When the guidewire conduit 150 is translucent, the guidewire conduit 150 is configured for viewing the guidewire 102 while distally feeding the guidewire 102 out of the guidewire-management device 100 or 300 or proximally feeding the guidewire 102 into the guidewire-management device 100 or 300.

FIG. 5 illustrates the ball end of the guidewire 102 distal to a plug 152 in the guidewire conduit 150 in accordance with some embodiments.

The guidewire conduit 150 has a proximal portion including the plug 152 configured to stop the ball end of the guidewire 102 from passing through what would otherwise be an opening in a proximal end of the guidewire conduit 150. Alternatively, the plug 152 is simply a crimped portion of the guidewire conduit 150 with the same effect. Stopping the ball end of the guidewire 102 from passing through such an opening prevents the tip of the guidewire 102 from completely passing through the first sleeve 110 and reforming the 'J'-shaped tip when proximally feeding the guidewire 102 into the guidewire-management device 100 or 300.

Adverting to FIGS. 6-16 to describe some of the unique features of at least the guidewire-management devices 600, 700, 900, 1200, 1300, and 1500, the guidewire-management device 600, 700, 900, 1200, 1300, or 1500 includes a handle 640, 740, 940, 1240, 1340, or 1540, the guidewire 102, the first sleeve 610, 710, 910, 1210, 1310, or 1510 formed in a distal portion of the handle 640, 740, 940, 1240, 1340, or 1540, the second sleeve 620, 720, 920, 1220, 1320, or 1520 formed in a proximal portion of the handle 640, 740, 940, 1240, 1340, or 1540, and a thumb wheel 642, 742, 942, 1242, 1342, or 1542 disposed under the guidewire 102 between the first sleeve 610, 710, 910, 1210, 1310, or 1510 and the second sleeve 620, 720, 920, 1220, 1320, or 1520.

The handle 640, 740, 940, 1240, 1340, or 1540 is ambidextrous in that it is configured to be held in either a right or left hand of a clinician. In addition, the handle 640, 740, 940, 1240, 1340, or 1540 is configured to be held in at least two different modes. The first mode, in which the clinician holds the handle 640, 740, 940, 1240, 1340, or 1540 like a person might hold the handle of a hammer, is a general mode for handling the guidewire-management device 600, 700, 900, 1200, 1300, or 1500. The second mode, in which the clinician repositions his or her thumb over the thumb wheel 642, 742, 942, 1242, 1342, or 1542, is an operational mode for advancing the guidewire 102 out of the guidewire-management device 600, 700, 900, 1200, 1300, or 1500 or withdrawing the guidewire 102 into the guidewire-management device 600, 700, 900, 1200, 1300, or 1500. Notwithstanding the foregoing, some clinicians might find it comfortable to hold the handle 640, 740, 940, 1240, 1340, or 1540 like a person might hold the barrel of a flashlight, thereby accessing both the first and second modes with less hand movement.

The handle 640, 1340, or 1540 includes a channel 641, 1341, or 1541 configured to hold a conduit therein. As set forth below, the conduit can be the guidewire conduit 1350 of the guidewire-management device 1300, the guidewire-casing conduit 1550 of the guidewire-management device 1500, or the like. Advantageously, such a channel can hold a conduit in a coiled configuration, thereby packing an otherwise elongate conduit into a compact space. While only the handles 640, 1340, and 1540 are shown with channels, any handle of the handles 740, 940, and 1240 can include a channel configured to hold a conduit. In addition, the handle 640, 1340, or 1540 need not include the channel 641, 1341, or 1541.

Notwithstanding possible differences in one or more design elements, the first sleeve 910, 1210, 1310, or 1510 is similar to the first sleeve 110, 610, or 710 set forth above. As such, the description set forth above for the first sleeves 110, 610, and 710 should be understood to extend to the first sleeves 910, 1210, 1310, and 1510 as if the first sleeves 910, 1210, 1310, and 1510 were included in the description of the first sleeves 110, 610, and 710.

Notwithstanding possible differences in one or more design elements, the second sleeve 920, 1220, 1320, or 1520 is similar to the second sleeve 120, 620, or 720 set forth above. As such, the description set forth above for the second sleeves 120, 620, and 720 should be understood to extend to the second sleeves 920, 1220, 1320, and 1520 as if the second sleeves 920, 1220, 1320, and 1520 were included in the description of the second sleeves 120, 620, and 720.

The thumb wheel 642, 742, 942, 1242, 1342, or 1542 can be rotatably mounted on an axle fixedly coupled to each side of the handle 640, 740, 940, 1240, 1340, or 1540 such that the thumb wheel 642, 742, 942, 1242, 1342, or 1542 rotates relative to both the axle and the handle 640, 740, 940, 1240, 1340, or 1540. Alternatively, the thumb wheel 642, 742, 942, 1242, 1342, or 1542 can include the axle (e.g., as a unitary piece) or be fixedly mounted on the axle, which, in turn, is rotatably coupled to each side of the handle 640, 740, 940, 1240, 1340, or 1540 such that a combination of the thumb wheel 642, 742, 942, 1242, 1342, or 1542 and the axle rotates with respect to the handle 640, 740, 940, 1240, 1340, or 1540. The thumb wheel 642, 742, 942, 1242, 1342, or 1542 is configured to assist in distally feeding the guidewire 102 out of the guidewire-management device 600, 700, 900, 1200, 1300, or 1500 by way of the first sleeve 610, 710, 910, 1210, 1310, or 1510. The thumb wheel 642, 742, 942, 1242, 1342, or 1542 is also configured to assist in proximally feeding the guidewire 102 into the guidewire-management device 600, 700, 900, 1200, 1300, or 1500 by way of the first sleeve 610, 710, 910, 1210, 1310, or 1510.

A method for distally feeding, or advancing, the guidewire 102 out of the guidewire-management device 600, 700, 900, 1200, 1300, or 1500 is set forth below. A method for proximally feeding, or withdrawing, the guidewire 102 into the guidewire-management device 600, 700, 900, 1200, 1300, or 1500 is also set forth below.

Adverting to FIGS. 9-12 to describe some of the unique features of at least the guidewire-management device 900 or 1200, the guidewire-management device 900 or 1200 includes a first split sleeve 911 or 1211 in the distal portion of the handle 940 or 1240.

The first split sleeve 911 or 1211 splits off the first sleeve 910 or 1210 in the distal portion of the handle 940 or 1240. Like the lumen of the first sleeve 110, 610, or 710 set forth above, as well as that of the first sleeve 910 or 1210 by extension, the first split sleeve 911 or 1211 is configured with a lumen. Indeed, the lumen of the first split sleeve 911 or 1211 splits or furcates from the lumen of the first sleeve 910 or 1210, thereby forming a bifurcated lumen between the first sleeve 910 or 1210 and the first split sleeve 911 or 1211 in the distal portion of the handle 940 or 1240. Whereas the first sleeve 910 or 1210 is configured for at least distally feeding the guidewire 102 out of the guidewire-management device 900 or 1200, the first split sleeve 911 or 1211 is configured for discharging the splittable casing 904 that splits off the guidewire 102 while distally feeding the guidewire 102 out of the guidewire-management device 900 or 1200. In fact, the bifurcated lumen between the first sleeve 910 or 1210 and the first split sleeve 911 or 1211 is configured to facilitate splitting the splittable casing 904 off the guidewire 102 while distally feeding the guidewire 102 out of the guidewire-management device 900 or 1200.

Adverting to FIG. 12 to describe some of the unique features of at least the guidewire-management device 1200, the guidewire-management device 1200 includes a flexible membrane 1206 extending from the distal portion of the guidewire-management device 1200, over the thumb wheel 1242, and to the proximal portion of the guidewire-management device 1200. Indeed, the membrane 1206 can be coupled to a portion of the first sleeve 1210 in the distal portion of the guidewire-management device 1200 and a portion of the second sleeve 1220 in the proximal portion of the guidewire-management device 1200.

The membrane 1206 is configured for distally feeding the guidewire 102 out of the guidewire-management device 1200 or proximally feeding the guidewire 102 into the guidewire-management device 1200. The membrane 1206 has sufficient flexibility for a medial portion of the membrane 1206 to be pressed down onto a proximal portion of the thumb wheel 1242, distally moved when the thumb wheel 1242 is rolled, and released back into an equilibrium state of the membrane 1206 for one or more additional rounds of the foregoing. Likewise, the membrane 1206 has sufficient flexibility for the medial portion of the membrane 1206 to be pressed down onto a distal portion of the thumb wheel 1242, proximally moved when the thumb wheel 1242 is rolled, and released back into the equilibrium state of the membrane 1206 for one or more additional rounds of the foregoing.

The membrane 1206 can have a low durometer, a degree of tackiness, or the like to facilitate gripping the guidewire 102 or a combination of the guidewire 102 within the bag 104 or splittable casing 904 for distally feeding the guidewire 102 out of the guidewire-management device 1200 or proximally feeding the guidewire 102 into the guidewire-management device 1200. As shown in FIG. 12, for example, the combination of the guidewire 102 within the splittable casing 904 is disposed between the membrane 1206 and the thumb wheel 1242 of the guidewire-management device 1200. When the medial portion of the membrane 1206 is pressed down onto the proximal or distal portion of the thumb wheel 1242, the combination of the guidewire 102 within the splittable casing 904 is also pressed down onto the proximal or distal portion of the thumb wheel 1242. When the thumb wheel 1242 is subsequently rolled, the combination of the guidewire 102 within the splittable casing 904 is distally or proximally moved with the medial portion of the membrane 1206. And when the medial portion of the membrane 1206 is released back into the equilibrium state of the membrane 1206, the combination of the guidewire 102 within the splittable casing 904 is also released. In this way, one or more additional rounds of the foregoing can distally feed the guidewire 102 out of the guidewire-management device 1200 or proximally feed the guidewire 102 into the guidewire-management device 1200.

Adverting to FIGS. 13 and 14 to describe some of the unique features of at least the guidewire-management device 1300, the guidewire-management device 1300 includes a guidewire conduit 1350 coupled to the second sleeve 1320 and a casing conduit 1354 coupled to both a first split sleeve 1311 in the distal portion of the handle 1340 and a second split sleeve 1321 in the proximal portion of the handle 1340.

Notwithstanding possible differences in one or more design elements, the first split sleeve 1311 is similar to the first split sleeve 911 or 1211 set forth above. As such, the description set forth above for the first split sleeves 911 and 1211 should be understood to extend to the first split sleeve 1311 as if the first split sleeve 1311 were included in the description of the first split sleeves 911 or 1211.

The second split sleeve 1321 splits off the second sleeve 1320 in the distal portion of the handle 1340. Like the lumen of the second sleeve 120, 620, or 720 set forth above, as well as that of the second sleeve 1320 by extension, the second split sleeve 1321 is configured with a lumen. Indeed, the lumen of the second split sleeve 1321 splits or furcates from the lumen of the second sleeve 1320, thereby forming a bifurcated lumen between the second sleeve 1320 and the second split sleeve 1321 in the distal portion of the handle 1340. Similar to the channel 1341 of the handle 1340, which channel 1341 is configured to hold the guidewire conduit 1350 therein, the second split sleeve 1321 is configured to hold the casing conduit 1354 therein.

As set forth above, the thumb wheel 1342 is configured to assist in distally feeding the guidewire 102 out of the guidewire-management device 1300 by way of the first sleeve 1310. In concert with the thumb wheel 1342, the guidewire conduit 1350 is configured to distally feed the guidewire 102, or, more specifically, the guidewire 102 disposed in the splittable casing 904, into the second sleeve 1320. The guidewire conduit 1350 can be opaque or translucent depending upon a chosen polymeric material. When the guidewire conduit 1350 is translucent, the guidewire conduit 1350 is configured for viewing the guidewire 102 while distally feeding the guidewire 102 into the second sleeve 1320. In addition, the casing conduit 1354 is configured to collect therein the splittable casing 904 that splits off the guidewire 102 while distally feeding the guidewire 102 out of the guidewire-management device 1300. Like the guidewire conduit 1350, the casing conduit 1354 can be opaque or translucent depending upon a chosen polymeric material. When the casing conduit 1354 is translucent, the casing conduit 1354 is configured for viewing the splittable casing 904 that splits off the guidewire 102 and into the casing conduit 1354 while distally feeding the guidewire 102 out of the guidewire-management device 1300.

As further set forth above, the thumb wheel 1342 is also configured to assist in proximally feeding the guidewire 102 into the guidewire-management device 1300 by way of the first sleeve 1310. In concert with the thumb wheel 1342, the casing conduit 1354 is configured to feed the splittable casing 904 that split off the guidewire 102 while distally feeding the guidewire 102 out of the guidewire-management device 1300 into the first sleeve 1310 for combination with the guidewire 102 as the guidewire 102 is proximally fed into the guidewire-management device 1300. Again, the casing conduit 1354 can be opaque or translucent. When the casing conduit 1354 is translucent, the casing conduit 1354 is configured for viewing the splittable casing 904 while proximally feeding the splittable casing 904 into the guidewire-management device 1300 for combination with the guidewire 102. The guidewire conduit 1350 is configured to collect therein the combination of the guidewire 102 and splittable casing 904, preferably, the guidewire 102 redisposed in the splittable casing 904, while proximally feeding the guidewire 102 into the guidewire-management device 1300. Again, the guidewire conduit 1350 can be opaque or translucent. When the guidewire conduit 1350 is translucent, the guidewire conduit 1350 is configured for viewing the combination of the guidewire 102 and splittable casing 904 while proximally feeding the guidewire 102 into the guidewire-management device 1300.

Adverting to FIGS. 15 and 16 to describe some of the unique features of at least the guidewire-management device 1500, the guidewire-management device 1500 includes a guidewire-casing conduit 1550 coupled to both the second sleeve 1520 and a first split sleeve 1511 in the distal portion of the handle 1540. The handle 1540 can include the channel 1541 configured to hold the guidewire-casing conduit 1550 therein when the guidewire-casing conduit 1550 is in a coiled configuration like that shown.

Notwithstanding possible differences in one or more design elements, the first split sleeve 1511 is similar to the first split sleeve 911 or 1211 set forth above. As such, the description set forth above for the first split sleeves 911 and 1211 should be understood to extend to the first split sleeve 1511 as if the first split sleeve 1511 were included in the description of the first split sleeves 911 or 1211.

As set forth above, the thumb wheel 1542 is configured to assist in distally feeding the guidewire 102 out of the guidewire-management device 1500 by way of the first sleeve 1510. In concert with the thumb wheel 1542, the guidewire-casing conduit 1550 is configured to distally feed the guidewire 102, or, more specifically, the guidewire 102 disposed in the splittable casing 904, into the second sleeve 1520. The guidewire-casing conduit 1550 can be opaque or translucent depending upon a chosen polymeric material. When the guidewire-casing conduit 1550 is translucent, the guidewire-casing conduit 1550 is configured for viewing the guidewire 102 while distally feeding the guidewire 102 into the second sleeve 1520. In addition, the guidewire-casing conduit 1550 is configured to collect therein the splittable casing 904 that splits off the guidewire 102 while distally feeding the guidewire 102 out of the guidewire-management device 1500. A distal end of the splittable casing 904 that splits off the guidewire 102 is configured to chase the ball end of the guidewire 102 around the guidewire-casing conduit 1550 while distally feeding the guidewire 102 out of the guidewire-management device 1500. Indeed, when the guidewire-casing conduit 1550 is translucent, the guidewire-casing conduit 1550 is configured for viewing the splittable casing 904 chase the ball end of the guidewire 102 around the guidewire-casing conduit 1550 while distally feeding the guidewire 102 out of the guidewire-management device 1500.

As further set forth above, the thumb wheel 1542 is also configured to assist in proximally feeding the guidewire 102 into the guidewire-management device 1500 by way of the first sleeve 1510. In concert with the thumb wheel 1542, the guidewire-casing conduit 1550 is configured to feed the splittable casing 904 that split off the guidewire 102 while distally feeding the guidewire 102 out of the guidewire-management device 1500 into the first sleeve 1510 for combination with the guidewire 102 as the guidewire is proximally fed into the guidewire-management device 1500. Again, the guidewire-casing conduit 1550 can be opaque or translucent. When the guidewire-casing conduit 1550 is translucent, the guidewire-casing conduit 1550 is configured for viewing the splittable casing 904 while proximally feeding the splittable casing 904 into the guidewire-management device 1500 for combination with the guidewire 102. The guidewire-casing conduit 1550 is configured to collect therein the combination of the guidewire 102 and splittable casing 904, preferably, the guidewire 102 redisposed in the splittable casing 904, while proximally feeding the guidewire 102 into the guidewire-management device 1500. When the guidewire-casing conduit 1550 is translucent, the guidewire-casing conduit 1550 is configured for viewing the combination of the guidewire 102 and splittable casing 904 while proximally feeding the guidewire 102 into the guidewire-management device 1500.

Lastly, FIG. 17 provides a side view of an assembly 1700 of the guidewire-management device 1500 coupled with a catheter assembly 1702 in accordance with some embodiments. With Luer connectors of the guidewire-management device 1500 and the catheter assembly 1702 coupled as shown, single-handed guidewire management while holding the assembly 1700 by the handle 1540 of the guidewire-management device 1500 is enabled.

Methods

A method of the guidewire-management device 100, 300, or 600 includes a connecting step of connecting the first sleeve 110 or 610 of the guidewire-management device 100, 300, or 600 to a hub of a medical device (e.g., a hollow needle) inserted into an insertion site of a patient.

The method further includes an advancing step of advancing the guidewire 102 of the guidewire-management device 100, 300, or 600 from the first sleeve 110 or 610 through the hub of the medical device and into the insertion site of the patient. The seal (e.g., the 'O'-ring 114 or 714) in the first sleeve 110 or 610 blocks fluid (e.g., air) from escaping the guidewire-management device 100, 300, or 600 when advancing the guidewire 102 through the hub of the medical device and into the insertion site of the patient.

The advancing step can include pinching the guidewire 102 within the sterile barrier 104 or 304 and advancing the guidewire 102 into the first sleeve 110 by hand. The advancing can alternatively include pressing the guidewire 102 within the sterile barrier 104 onto the thumb wheel 742 and rolling the thumb wheel 742 to advance the guidewire 102 into the first sleeve 610.

Indeed, the guidewire 102 can be advanced into the first sleeve 110 or 610 and out of the guidewire-management device 100 or 600 by pinching a combination of the guidewire 102 within the bag 104 or pressing the guidewire 102 within the bag 104 against the thumb wheel 742, advancing the guidewire 102 into the first sleeve 110 by hand or by rolling the thumb wheel 742, releasing the combination of the guidewire 102 within the bag 104, and repeating the foregoing as necessary. The guidewire 102 can be advanced into the first sleeve 110 and out of the guidewire-management device 300 by pinching a combination of the guidewire 102 within the boot 304, advancing the guidewire 102 into the first sleeve 110 by hand, releasing the combination of the guidewire 102 within the boot 304, and repeating the foregoing as necessary.

The method can further include a ceasing step of ceasing to advance the guidewire 102 into the insertion site of the patient when the ball end of the guidewire 102 is captured in the constriction 124 of the bore 122 in the second sleeve 120 of the guidewire-management device 100 or 300. Likewise, the ceasing step can include ceasing to advance the guidewire 102 into the insertion site of the patient when the ball end of the guidewire 102 is captured in the recess 724 in the second sleeve 620 of the guidewire-management device 600.

The method further includes withdrawing the guidewire 102 from the insertion site of the patient through the hub of the medical device and into the first sleeve 110 or 610. The seal (e.g., the 'O'-ring 114 or 714) in the first sleeve 110 or 610 blocks fluid (e.g., blood) from entering the guidewire-management device 100, 300, or 600 when withdrawing the guidewire 102 from the insertion site.

Indeed, the guidewire 102 can be withdrawn into the guidewire-management device 100 or 600 through the first sleeve 110 or 610 by pinching the combination of the guidewire 102 within the bag 104 or pressing the guidewire 102 within the bag 104 against the thumb wheel 742, withdrawing the guidewire 102 from the first sleeve 110 by hand or by rolling the thumb wheel 742, releasing the combination of the guidewire 102 within the bag 104, and repeating the foregoing as necessary. The guidewire 102 can be withdrawn into the guidewire-management device 300 through the first sleeve 110 by pinching the combination of the guidewire 102 within the boot 304, withdrawing the guidewire 102 from the first sleeve 110 by hand, releasing the combination of the guidewire 102 within the boot 304, and repeating the foregoing as necessary.

The method can further include ceasing to withdraw the guidewire 102 from the insertion site of the patient when the proximal end or the ball end of the guidewire 102 abuts the plug 152 in the proximal portion of the guidewire conduit 150 of the guidewire-management device 100 or 300.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A guidewire-management device, comprising:
   a guidewire;
   a first sleeve configured for distally feeding the guidewire out of the guidewire-management device or proximally feeding the guidewire into the guidewire-management device;
   a second sleeve proximal of the first sleeve configured for feeding the guidewire in concert with the first sleeve, at least a length of the guidewire extending between the first sleeve and the second sleeve is disposed within a sterile barrier configured to maintain sterility of the guidewire, the sterile barrier being a splittable casing configured to split off the guidewire while distally feeding the guidewire out of the guidewire-management device; and
   a tubular conduit coupled with the first sleeve, the tubular conduit configured to receive a split-off portion of the splittable casing therein.

2. The guidewire-management device of claim 1, wherein the first sleeve has a distal portion configured as a male connector with a Luer taper for connecting the first sleeve to a complementary female connector.

3. The guidewire-management device of claim 1, wherein the first sleeve is configured to straighten the guidewire when proximally feeding the guidewire into the guidewire-management device.

4. The guidewire-management device of claim 1, wherein the first sleeve includes a seal configured to block fluid from entering or escaping the guidewire-management device when proximally feeding the guidewire into the guidewire-management device.

5. The guidewire-management device of claim 1, wherein the first sleeve has a proximal portion including a bore configured to house a distal portion of the sterile barrier.

6. The guidewire-management device of claim 1, wherein the second sleeve has a distal portion including a bore configured to house a proximal portion of the sterile barrier.

7. The guidewire-management device of claim 1, wherein the second sleeve has a proximal portion including a bore configured to stop an end of the guidewire from completely passing through the second sleeve.

8. The guidewire-management device of claim 1, wherein the guidewire has a distal portion including a T-shaped tip configured to straighten as the 'J'-shaped tip of the guidewire enters the first sleeve when proximally feeding the guidewire into the guidewire-management device.

9. The guidewire-management device of claim 1, wherein the guidewire has a proximal portion including a ball end configured to stop the guidewire from completely passing through the second sleeve.

10. The guidewire-management device of claim 1, wherein the guidewire-management device is configured to redispose the splittable casing over the guidewire while proximally feeding the guidewire into of the guidewire-management device.

11. A guidewire-management device, comprising:
    a handle;
    a guidewire;
    a first sleeve formed in a distal portion of the handle;
    a second sleeve formed in a proximal portion of the handle, at least a length of the guidewire extending between the first sleeve and the second sleeve is disposed within a sterile barrier configured to maintain sterility of the guidewire, the sterile barrier being a splittable casing configured to split off the guidewire while distally feeding the guidewire out of the guidewire-management device;
    a thumb wheel disposed under the guidewire between the first sleeve and the second sleeve configured to assist in distally feeding the guidewire out of the guidewire-management device by way of the first sleeve and proximally feeding the guidewire into the guidewire-management device by way of the first sleeve, wherein while proximally feeding the guidewire into the guidewire-management device, a split-off portion of the splittable casing is recombined with the guidewire; and
    a tubular casing conduit coupled with the first sleeve, the tubular casing conduit configured to receive the split-off portion when the split-off portion is split off the guidewire.

12. The guidewire-management device of claim 11, wherein the first sleeve has a distal portion configured as a male connector with a Luer taper for connecting the first sleeve to a complementary female connector.

13. The guidewire-management device of claim 11, wherein the first sleeve is configured to straighten a T-shaped tip in a distal portion of the guidewire as the 'J'-shaped tip of the guidewire enters the first sleeve when proximally feeding the guidewire into the guidewire-management device.

14. The guidewire-management device of claim 11, wherein the second sleeve has a proximal portion including a bore with a constriction configured to capture a ball end of the guidewire and stop the guidewire from completely passing through the second sleeve.

15. The guidewire-management device of claim 11, wherein the splittable casing is over an entirety of the guidewire excepting that within or distal to the first sleeve.

16. The guidewire-management device of claim 11, further comprising:
    a guidewire conduit coupled to the second sleeve configured to distally feed the guidewire into the second sleeve; and
    the tubular casing conduit coupled to both a first split sleeve in the distal portion of the handle and a second split sleeve in the proximal portion of the handle, the tubular casing conduit configured to collect therein the split-off portion.

17. The guidewire-management device of claim 16, wherein the handle includes a channel configured to hold the guidewire conduit therein when the guidewire conduit is in a coiled configuration.

18. The guidewire-management device of claim 11, wherein the tubular casing conduit includes a guidewire-casing conduit coupled to both the second sleeve and a first split sleeve in the distal portion of the handle, the guidewire-casing conduit configured to distally feed the guidewire into the second sleeve, as well as collect therein by way of the first split sleeve the split-off portion.

19. The guidewire-management device of claim 18, wherein a distal end of the splittable casing that splits off the guidewire is configured to chase a proximal end of the guidewire around the guidewire-casing conduit while distally feeding the guidewire out of the guidewire-management device.

20. The guidewire-management device of claim 18, wherein the handle includes a channel configured to hold the guidewire-casing conduit therein when the guidewire-casing conduit is in a coiled configuration.

21. The guidewire-management device of claim 11, further comprising a flexible membrane extending from the distal portion of the handle, over the thumb wheel, and to the proximal portion of the handle configured to be pressed down onto the thumb wheel for distally feeding the guidewire out of the guidewire-management device or proximally feeding the guidewire into the guidewire-management device.

* * * * *